US012378575B2

(12) United States Patent
Yovcheva et al.

(10) Patent No.: US 12,378,575 B2
(45) Date of Patent: Aug. 5, 2025

(54) CHEMICALLY-DEFINED BACULOVIRUS EXPRESSION SYSTEM

(71) Applicant: LIFE TECHNOLOGIES CORPORATION, Carlsbad, CA (US)

(72) Inventors: Maya Yovcheva, Demascus, MD (US); Jonathan Zmuda, Frederick, MD (US); Sara Barnes, Germantown, MD (US); Chang Choi, San Diego, CA (US); Kenneth Thompson, Burtonsville, MD (US)

(73) Assignee: Life Technologies Corporation, Carlsbad, CA (US)

( * ) Notice: Subject to any disclaimer, the term of this patent is extended or adjusted under 35 U.S.C. 154(b) by 1118 days.

(21) Appl. No.: 17/046,693

(22) PCT Filed: Apr. 11, 2019

(86) PCT No.: PCT/US2019/027108
§ 371 (c)(1),
(2) Date: Oct. 9, 2020

(87) PCT Pub. No.: WO2019/200184
PCT Pub. Date: Oct. 17, 2019

(65) Prior Publication Data
US 2021/0310024 A1  Oct. 7, 2021

Related U.S. Application Data

(60) Provisional application No. 62/656,868, filed on Apr. 12, 2018.

(51) Int. Cl.
*C12N 15/86* (2006.01)
*C12N 5/07* (2010.01)
*C12N 7/00* (2006.01)
*C12P 21/00* (2006.01)

(52) U.S. Cl.
CPC ........... *C12N 15/86* (2013.01); *C12N 5/0601* (2013.01); *C12N 7/00* (2013.01); *C12P 21/00* (2013.01); *C12N 2500/02* (2013.01); *C12N 2500/05* (2013.01); *C12N 2500/34* (2013.01); *C12N 2500/38* (2013.01); *C12N 2510/00* (2013.01); *C12N 2710/14143* (2013.01); *C12N 2710/14151* (2013.01)

(58) Field of Classification Search
CPC ....... A61P 31/12; C12N 7/00; C12N 2501/70; C07K 2319/33
USPC ...................................................... 435/69.1
See application file for complete search history.

(56) References Cited

U.S. PATENT DOCUMENTS

2004/0086965 A1    5/2004    Claus et al.

FOREIGN PATENT DOCUMENTS

CN     104911143 A    9/2015
WO     WO-2014110440 A1    7/2014

OTHER PUBLICATIONS

Mitsuhashi J., "Preliminary Formulation of a Chemically Defined Medium for Insect Cell Cultures," Methods in Cell Science, Dec. 1996, vol. 18, pp. 293-298.
Database WPI Week 201609, Thomson Scientific, London, GB; AN 2016-06473H, XP002792439.
Deparis V, et al., "Promoting effect of rapeseed proteins and peptides on Sf9 insect cell growth", Cytotechnology, Kluwer Academic Publishers, DO, XP019236787, vol. 42, No. 2, Jun. 1, 2003 (Jun. 1, 2003), pp. 75-85.
Ikonomou L, et al., "Insect Cell Culture for Industrial Production of Recombinant Proteins", Applied Microbiology and Biotechnology, Springer, DE, vol. 62, No. 1, Jul. 1, 2003 (Jul. 1, 2003), pp. 1-20.
International Search Report and Written Opinion for Application No. PCT/US2019/027108, mailed Jul. 15, 2019, 13 pages.
Klaassen C.H, et al., "Large-Scale Production and Purification of Functional Recombinant Bovine Rhodopsin with the Use of the Baculovirus Expression System", Biochem J., XP055598981, vol. 342, Jan. 1, 1999 (Jan. 1, 1999), pp. 293-300.
Marunouchi T, et al., "Substitution of inosine for yeastolate in the culture medium for*Drosophila* cells", XP055598926, vol. 14, No. 12, Jan. 1, 1978 (Jan. 1, 1978), pp. 1010-1014.
Mendonça R.Z, et al., "Effect of bioactive peptides isolated from yeastolate, lactalbumin and NZCase in the insect cell growth", Bioprocess and Biosystems Engineering, Springer, Berlin, DE, XP019518081, vol. 30, No. 3, Feb. 4, 2007 (Feb. 4, 2007), pp. 157-164.
Peng Y, et al., "The Histone Deacetylase Inhibitor Sodium Butyrate Inhibits Baculovirus-Mediated Transgene Expression in Sf9 Cells", Journal of Biotechnology, Elsevier, Amsterdam, NL, XP022184734, vol. 131, No. 2, Aug. 6, 2007 (Aug. 6, 2007), pp. 180-187.
Yovcheva M, et al., "A Chemically-Defined Baculovirus-Based Expression System for Enhanced Protein Production in Sf9 Cells", Thermo Fisher Scientific Inc., 2017, XP002792438, Retrieved from the Internet: https://assets.thermofisher.com/TFS-Assets/BID/posters/chemically-defined-baculovirus-expression-system-sf9-cells-poster.pdf, [retrieved on Jun. 25, 2019].

(Continued)

*Primary Examiner* — Robert B Mondesi
*Assistant Examiner* — Mohammad Y Meah
(74) *Attorney, Agent, or Firm* — Caroline D. Belt

(57) ABSTRACT

The present disclosure is related generally to systems and methods for high level expression of recombinant proteins from baculovirus in insect cells. In particular, the methods and systems described herein allow for high levels of baculovirus production in insect cells and/or high levels of protein production in insect cells using a chemically-defined, yeast lysate-free insect cell medium. The disclosure also relates to compositions and kits for culturing, transfecting, and/or producing recombinant protein in insect cells.

18 Claims, 10 Drawing Sheets

(56) References Cited

OTHER PUBLICATIONS

Song S., et al., "Construction of Baculovirus Vector with Cytomegalovirus Promoter to Express eGFP in Primary Chicken Embryo Cells," Acta Microbiologica Sinica, Jun. 4, 2013, vol. 53, No. 6, pp. 586-595.

Wu H., et al., "Experimental Study on Baculovirus Vector-Mediated Sodium Iodide Transporter Gene Radiation Therapy for Liver Cancer," Journal of Shanghai Jiao Tong University (Medical Science), May 28, 2012, vol. 32, No. 5, pp. 560-566.

Luciferase Activity Measured by NFκB Activation

CHEMICALLY-DEFINED BACULOVIRUS EXPRESSION SYSTEM

CROSS-REFERENCE TO RELATED APPLICATION

This application is a 35 USC 371 National Phase filing of International Application No. PCT/US2019/027108 filed Apr. 11, 2019, and claims priority to U.S. Provisional Application No. 62/656,868, filed Apr. 12, 2018, each of which disclosure is herein incorporated by reference in its entirety.

BACKGROUND

Cell culture media provide the nutrients necessary to maintain and grow cells in a controlled, artificial and in vitro environment. Characteristics and formulations of cell culture media vary depending upon the particular cellular requirements. Important parameters include osmolarity, pH, and nutrient compositions.

Cell culture medium formulations have been well documented in the literature and a large number of media are commercially available. Typical components of cell culture media include amino acids, organic and inorganic salts, vitamins, trace metals, sugars, lipids and nucleic acids, the types and amounts of which may vary depending upon the particular requirements of a given species, cell or tissue type.

Medium formulations have been used to cultivate a number of cell types including animal, plant and bacterial cells. Cultivated cells have many uses including the study of physiological processes and the production of useful biological substances. Examples of such useful products include monoclonal antibodies, hormones, growth factors, enzymes and the like. Such products have many commercial and therapeutic applications and, with the advent of recombinant DNA technology, cells can be engineered to produce large quantities of these products. Cultured cells are also routinely used for the isolation, identification and growth of viruses that can be used as vectors and/or vaccines. Thus, the ability to cultivate cells in vitro is not only important for the study of cell physiology, but is also necessary for the production of useful substances that may not otherwise be obtained by cost-effective means.

Insect cell culture is commonly used for production of recombinant proteins. Unlike prokaryotic cells, insect cells are able to express large quantities of protein with complex post-translational modifications, for both basic research and large-scale production. Insect cells are also a suitable host for expression of multimeric proteins, virus-like particles, and proteins that are toxic to mammalian cells. Several FDA-approved vaccines and therapies use baculovirus expression in insect cells, including CERVARIX™, PROVENGE™, GLYBERA™, and FLUBLOK™. In particular, Sf9 cells are commonly used to isolate and propagate recombinant baculoviral stocks and to produce recombinant proteins. The original Sf9 cells were cloned from the parental IPLBSF-21 (Sf21) cell line that was derived from the pupal ovarian tissue of the fall army worm, *Spodoptera frugiperda*.

Typically, cell culture media formulations are supplemented with a range of additives, including undefined components such as fetal bovine serum (FBS) (5-20% v/v) or extracts from animal embryos, organs or glands (0.5-10% v/v). Insect cell medium is often supplemented with yeast lysate, also called yeastolate. Yeastolate is a yeast extract obtained after the autolysis of yeast cells, such as brewer's yeast or baker's yeast, including *Saccharomyces cervisiae*. Yeastolate is a complex mixture, and the constituents responsible for promoting cell growth have not been determined.

Such chemically-undefined supplements serve several useful functions in cell culture media. For example, these supplements provide carriers or chelators for labile or water-insoluble nutrients; bind and neutralize toxic moieties; provide hormones and growth factors, protease inhibitors and essential, often unidentified or undefined low molecular weight nutrients; and protect cells from physical stress and damage. Thus, serum, organ/gland extracts, or yeast extracts are commonly used as relatively low-cost supplements to provide an optimal culture medium for the cultivation of cells.

Unfortunately, the use of serum, organ/gland extracts, or yeast extracts in tissue culture applications has several drawbacks. For example, the chemical compositions of these supplements and sera vary between lots, even from a single manufacturer. The supplements can also be contaminated with infectious agents (e.g., *Mycoplasma* and viruses) which can seriously undermine the health of the cultured cells and the quality of the final product. The use of undefined components from these sera or extracts also prevents the true definition and elucidation of the nutritional and hormonal requirements of the cultured cells. Finally and most importantly to those employing cell culture media in the industrial production of biological substances, serum, organ/gland extracts, or yeast extract supplementation of culture media can complicate and increase the costs of the purification of the desired substances from the culture media due to non-specific co-purification of serum or extract proteins.

There remains a need for chemically-defined, yeast lysate-free, serum-free, and animal product-free insect cell medium, as well as systems and methods for improved production of baculovirus and/or protein in cultivated insect cells.

SUMMARY

The present disclosure relates to, inter alia, a baculovirus expression system, various components thereof, and uses of the expression system and/or components thereof to produce baculovirus or protein. In some embodiments, a baculovirus expression system comprises:
 (a) a chemically-defined, yeast hydrolysate-free medium; and
 (b) a plurality of Sf9 cells.

In some embodiments, the baculovirus expression system further comprises a protein expression enhancer. In some embodiments, the protein expression enhancer comprises a histone deacetylase (HDAC) inhibitor. In some embodiments, the HDAC inhibitor is selected from apicidin, belinostat, CI-994, CRA-024781, curcumin, panobinostat, sodium butyrate, sodium phenylbutyrate, suberoylanilide hydroxamic acid, trichostatin A, and valproic acid. In some embodiments, the HDAC inhibitor is sodium butyrate, sodium phenylbutyrate, trichostatin A, or valproic acid.

In some embodiments, the baculovirus expression further comprises a transfection reagent. In some embodiments, the transfection reagent is a cationic lipid transfection reagent or a polymer-based transfection reagent.

In some embodiments, the medium is an insect cell medium.

In some embodiments, the plurality of Sf9 cells are capable of growing in suspension culture in the medium.

In some embodiments, the plurality of Sf9 cells are capable of high-density growth in the medium. In some embodiments, the Sf9 cells are capable of peak cell density of about $2\times10^6$ to about $2\times10^8$ cells per milliliter (cells/mL).

In some embodiments, the medium comprises an inorganic salt selected from a barium salt, a cadmium salt, a copper salt, a magnesium salt, a manganese salt, a nickel salt, a potassium salt, a calcium salt, a silver salt, a tin salt, a zirconium salt, a sodium salt, or combinations thereof.

In some embodiments, the medium comprises a vitamin selected from para-aminobenzoic acid, vitamin B12, biotin, choline, folic acid, inositol, nicotinic acid, niacinamide, pantothenic acid, pyridoxine, riboflavin, thiamine, a tocopherol, or combinations thereof.

In some embodiments, the baculovirus expression system further comprises a baculovirus vector.

The disclosure relates, in part, to a medium for insect cell culture comprising an inorganic salt selected from a barium salt, a cadmium salt, a copper salt, a magnesium salt, a manganese salt, a nickel salt, a potassium salt, a calcium salt, a silver salt, a tin salt, a zirconium salt, a sodium salt, or combinations thereof, and a vitamin. In some embodiments, the amount of inorganic salt is sufficient to support growth of insect cells. In some embodiments, the medium is a chemically-defined and yeast hydrolysate-free medium. In some embodiments, the medium does not comprise protein. In some embodiments, the medium does not comprise serum. In some embodiments, the medium does not comprise an ingredient derived from an animal.

In some embodiments, the vitamin is selected from para-aminobenzoic acid, vitamin B12, biotin, choline, folic acid, inositol, nicotinic acid, niacinamide, pantothenic acid, pyridoxine, riboflavin, thiamine, a tocopherol, or combinations thereof. In some embodiments, the amount of vitamin is sufficient to support growth of insect cells.

In some embodiments, the medium further comprises an amount of a sugar that is sufficient to support growth of insect cells. In some embodiments, the sugar is selected from maltose, sucrose, glucose, trehalose, fructose, mannose, lactose, galactose, dextrose, or combinations thereof.

In some embodiments, a method of growing insect cells comprises culturing insect cells in a medium as described herein.

The disclosure relates, in part, to a method of baculovirus production comprising:
 (a) culturing insect cells in a chemically-defined, yeast hydrolysate-free medium;
 (b) transfecting the cells with a bacmid; and
 (c) harvesting the virus from the insect cell culture.

In some embodiments, the cells are transfected using a cationic lipid transfection reagent or a polymer-based transfection reagent.

In some embodiments, the insect cells are Sf9 cells.

In some embodiments, the insect cells are in suspension culture.

In some embodiments, the transfection step is performed when the insect cells are present at a viable cell density between $1\times10^6$ cells per milliliter (cells/mL) and $2\times10^7$ cells/mL. In some embodiments, the transfection step is performed when the insect cells are ≥90% viable.

In some embodiments, the medium comprises an inorganic salt selected from a barium salt, a cadmium salt, a copper salt, a magnesium salt, a manganese salt, a nickel salt, a potassium salt, a calcium salt, a silver salt, a tin salt, a zirconium salt, or combinations thereof.

In some embodiments, the medium comprises a vitamin selected from para-aminobenzoic acid, vitamin B12, biotin, choline, folic acid, inositol, nicotinic acid, niacinamide, pantothenic acid, pyridoxine, riboflavin, thiamine, a tocopherol, or combinations thereof.

In some embodiments, the medium is not changed, replenished, replaced, or supplemented with fresh medium after the transfection step.

In some embodiments, the harvested baculovirus has a titer of at least $5\times10^7$ infectious virus particles per milliliter (IVP/mL). In some embodiments, the harvested baculovirus has a titer of at least $1\times10^8$ IVP/mL. In some embodiments, the harvested baculovirus has a titer of between $5\times10^7$ IVP/mL and $1\times10^{10}$ IVP/mL.

The disclosure relates, in part, to a method of protein production from a baculovirus comprising:
 (a) culturing insect cells in a chemically-defined, yeast hydrolysate-free medium; and
 (b) infecting the insect cells with a baculovirus that expresses the protein.

In some embodiments, a protein expression enhancer is added to the medium before step (b). In some embodiments, the protein expression enhancer is added at least 10 hours before infection. In some embodiments, the protein expression enhancer is added between 12 hours and 36 hours before infection. In some embodiments, the protein expression enhancer is added between 18 hours and 24 hours before infection.

In some embodiments, the protein expression enhancer comprises a histone deacetylase (HDAC) inhibitor. In some embodiments, the HDAC inhibitor is selected from apicidin, belinostat, CI-994, CRA-024781, curcumin, panobinostat, sodium butyrate, sodium phenylbutyrate, suberoylanilide hydroxamic acid, trichostatin A, and valproic acid. In some embodiments, the HDAC inhibitor is sodium butyrate, sodium phenylbutyrate, richostatin A, or valproic acid.

In some embodiments, the insect cells are Sf9 cells.

In some embodiments, the insect cells are capable of high-density growth in the medium. In some embodiments, the Sf9 cells are capable of peak cell density of about $2\times10^6$ to about $2\times10^8$ cells per milliliter (cells/mL).

In some embodiments, the insect cells are in suspension culture. In some embodiments, the insect cells are in adherent culture.

In some embodiments, the infection step is performed when the insect cells are present at a viable cell density of between $3\times10^6$ cells per milliliter (cells/mL) and $1\times10^7$ cells/mL. In some embodiments, the infection step is performed when the insect cells are ≥80% viable.

In some embodiments, the baculovirus used to infect the insect cells has a multiplicity of infection (MOI) between 1 and 10. In some embodiments, the baculovirus used to infect the insect cells has a MOI between 3 and 7. In some embodiments, the baculovirus used to infect the insect cells has a MOI of about 5.

In some embodiments, the method further comprises: (c) culturing the infected cells for a period of time to produce the protein.

In some embodiments, the method further comprises: (d) harvesting the protein.

In some embodiments, steps (a) through (d) take between 5 days and 15 days. In some embodiments, the protein is harvested about 24 hours to about 120 hours after infection.

In some embodiments, the medium is not replaced, replenished, or supplemented with fresh medium during protein production.

In some embodiments, the insect cells are in adherent culture. In some embodiments, the insect cells are in suspension culture.

Each of the aspects and embodiments described herein are capable of being used together, unless excluded either explicitly or clearly from the context of the embodiment or aspect.

DETAILED DESCRIPTION

I. Definitions

Figure 1A:
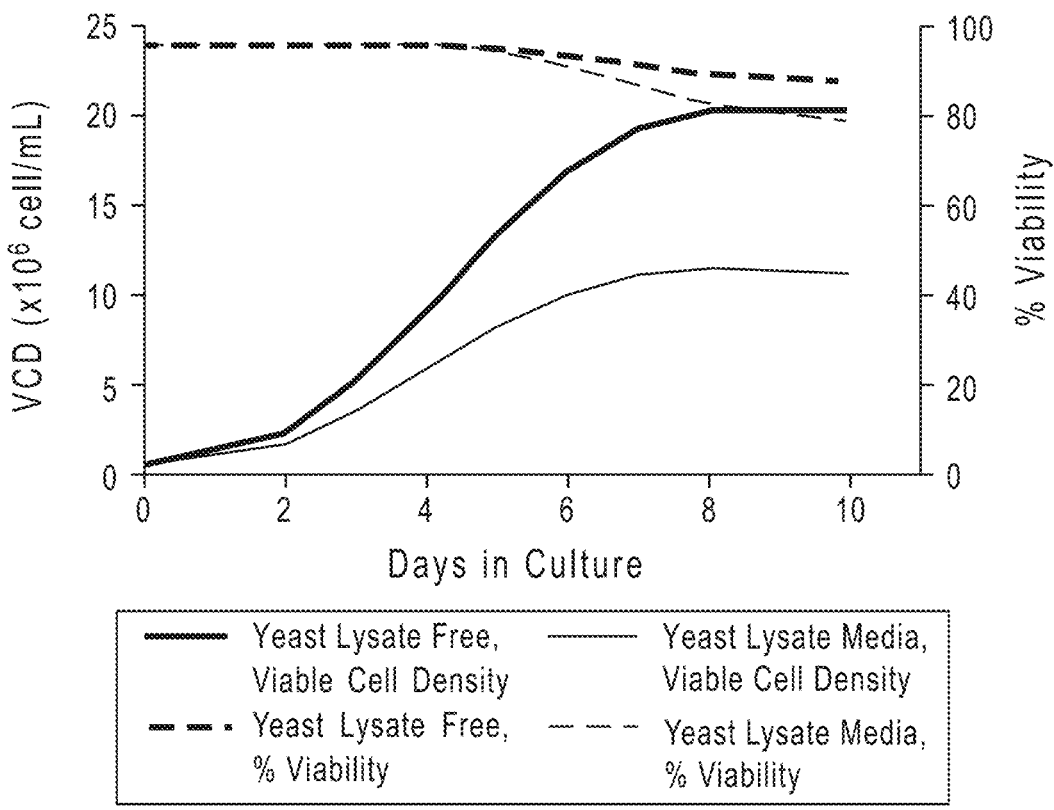
FIG. 1A is a line graph showing the viable cell density (VCD; solid lines) and percent viability (dashed lines) for Sf9 cells grown in chemically-defined, yeast lysate-free insect cell medium (heavy) or in insect cell medium containing yeast lysate (yeastolate; light).

The terms "a" or "an," as used in herein means one or more.

The term "cell" as used herein refers includes all types of eukaryotic and prokaryotic cells. In some embodiments, the term refers to eukaryotic cells, especially insect cells. In certain exemplary though non-limiting embodiments, the term "cell" is meant to refer to *Spodoptera frugiperda* cells, such as, e.g., Sf9 cells, or a variant thereof. A variant of an Sf9 cell includes, for example and without limitation, Sf9 cells that can grow in yeast lysate (yeastolate)-free medium, and/or Sf9 cells that can grow, proliferate and be transfected in suspension culture. A variant of an Sf9 cell includes, for example and without limitation, Sf9 cells that can be cultured at high density (e.g., ≥ about $2\times10^6$ cells/mL, ≥ about $5\times10^6$ cells/mL, ≥ about $2\times10^7$ cells/mL, or higher).

The phrase "capable of high density growth" when used in the context of culturing cells and conducting transfection and viral production workflows, generally refers to a known cell line, or a variant of a known cell line, that can be grown or cultured in an appropriate cell culture medium to peak cell densities of ≥ about $1\times10^6$ cells/mL, ≥ about $2\times10^6$ cells/mL, ≥ about $3\times10^6$ cells/mL, or even optionally ≥ about $4\times10^6$ cells/mL, or ≥ about $2\times10^7$ cells/mL, while still retaining the ability to be transfected at high efficiency. In some embodiments, such cells are also able to express a target protein at high levels (e.g., levels at or exceeding 200 μg/mL to up to about 1 mg/mL or more).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "yeast lysate" or "yeastolate" refers to an aqueous extract of yeast (e.g., baker's or brewer's yeast) which contains (usually undefined) mixtures of amino acids, peptides, polysaccharides, vitamins, and minerals. See, e.g., Shen et al., *Cytotechnology.* 2007 May; 54(1): 25-34, which is incorporated herein by reference in its entirety. Yeastolate may be ultra-filtered or not ultra-filtered.

The term "yeast lysate-free" or "yeastolate-free" as used herein refers to medium, in particular insect cell medium, which is free or substantially free of yeast lysate. Preferably, the medium is entirely free of yeast lysate. "Substantially free of yeast lysate" as used herein refers to media which contains less than about 1% yeast lysate by weight, contains only trace amounts of yeast lysate, or contains undetectable amounts of yeast lysate.

The term "serum-free" as used herein refers to medium which is free or substantially free of serum. "Substantially free of serum" as used herein refers to media which contains less than about 1% serum by weight, contains only trace amounts of serum, or contains undetectable amounts of serum.

The term "chemically-defined medium" as used herein refers to medium suitable for in vitro culture of cells, particularly eukaryotic cells, in which all of the chemical components and their concentrations are known.

The phrase "protein-free" culture medium refers to culture medium that contain no protein (e.g., no serum proteins such as serum albumin or attachment factors, nutritive proteins such as growth factors, or metal ion carrier proteins such as transferrin, ceruloplasmin, etc.). Preferably, if peptides are present, the peptides are smaller peptides, e.g., di- or tri-peptides. Preferably, peptides of deca-peptide length or greater are less than about 1%, more preferably less than about 0.1%, and even more preferably less than about 0.01% of the amino acids present in the protein free medium.

The term "animal derived" material as used herein refers to material that is derived in whole or in part from an animal source, including recombinant animal DNA or recombinant animal protein DNA.

The term "expression enhancer" generally refers to one or more liquid (preferably aqueous) additives used to supplement a culture medium formulation in accordance with the presently described embodiments, said additives being selected to improve the yield of expressed protein produced in a transient protein expression system in accordance with the presently described embodiments. The term encompasses any one or more of several compounds that affect cell cycle progression, inhibit apoptosis, slow cell growth and/or promote protein production. In the context of the present invention, the term "expression enhancers" generally refers to any one or more compounds added to a protein expression system, the presence of which enhances or promotes expression of a target protein by a factor of at least 2 fold up to about 10-fold above the expression level seen in the absence of such expression enhancer(s).

The term "bacmid" as used herein refers to a baculovirus vector that replicates in bacteria, but when transfected into insect cells allows production of baculovirus by the insect cells.

By "cell culture" or "culture" is meant the maintenance of cells in an artificial, in vitro environment.

By "cultivation" is meant the maintenance of cells in vitro under conditions favoring growth and/or differentiation and/ or or continued viability. "Cultivation" can be used interchangeably with "cell culture." Cultivation is assessed by number of viable cells/mL culture medium. Cultivation after introduction of a macromolecule preferably includes production of a product, for example, a protein product on a virus.

The term "replenishing, replacing, or supplementing medium" as used herein refers to adding a volume of fresh cell culture medium to medium that was already present in culture and/or replacing medium that was already present in culture with fresh medium, and/or supplementing medium already present in culture with new medium. Fresh medium is medium that does not contain the one or more macromolecules or compounds to be introduced into at least one cell or medium that has not been in contact with cells to support their growth on cultivation. The skilled artisan can determine whether there is an advantage from or a need to remove and/or replenish, replace or supplement medium by monitoring cell growth and/or viability by techniques known in the art, such as cell counting (manual or automated), trypan blue exclusion, production of protein or other substance, alamar blue assay, presence or concentration of one or more metabolic products, cell adhesion, morphological appearance, analysis of spent medium, etc. One or a combination of monitoring techniques can be used to determine whether the medium needs to be to support growth, introduction of at least one macromolecule and/or cultivation after introduction of at least one macromolecule.

"Recombinant protein" refers to protein that is encoded by a nucleic acid that is introduced into a host cell. The host cell expresses the nucleic acid. The term "expressing a nucleic acid" is synonymous with "expressing a protein from an RNA encoded by a nucleic acid. "Protein" as used herein broadly refers to polymerized amino acids, e.g., peptides, polypeptides, proteins, lipoproteins, glycoproteins, etc.

The term "protein yield" refers to the amount of protein expressed by cultured cells, and can be measured, for example, in terms of grams of protein produced per milliliter medium. If the protein is not secreted by the cells, the protein can be isolated from the interior of the cells by methods known to those of ordinary skill in the art. If the protein is secreted by the cells, the protein can be isolated from the culture medium by methods known to those of ordinary skill in the art. The amount of protein expressed by the cell can readily be determined by those of ordinary skill in the art. The protein may be a recombinant protein.

A "protein product" is a product associated with production or an action by a protein. A protein product may be a protein. A protein product may also be a product resulting from action of a protein by one or more other substances to produce a product. An example of such action is enzymatic action by a protein.

By "suspension culture" is meant cell culture in which the majority or all of cells in a culture vessel are present in suspension, and the minority or none of the cells in the culture vessel are attached to the vessel surface or to another surface within the vessel. Preferably, "suspension culture" has greater than 75% of the cells in the culture vessel are in suspension, not attached to a surface on or in the culture vessel. More preferably, a "suspension culture" has greater than 85% of the cells in the culture vessel are present in suspension, not attached to a surface on or in the culture vessel. Even more preferred is a "suspension culture" with greater than 95% of the cells in the culture vessel present in suspension, not attached to a surface on or in the culture vessel.

The medium, methods, kits and compositions of the present invention are suitable for monolayer (adherent) or suspension culture, transfection, and cultivation of cells, and for expression of protein in cells in monolayer or suspension culture. Preferably, the medium, methods, kits and compositions of the present invention are for suspension culture, transfection, and cultivation of cells, and for expression of protein product in cells in suspension culture.

By "culture vessel" is meant any container, for example, a glass, plastic, or metal container, that can provide an aseptic environment for culturing cells.

The phrases "cell culture medium, tissue culture medium," "culture medium" (plural "media" in each case) and "medium formulation" refer to a nutritive solution for cultivating cells or tissues. These phrases can be used interchangeably.

The term "combining" refers to the mixing or admixing of ingredients.

The term "trace element" or "trace element moiety" refers to a moiety which is present in a cell culture medium in only very low (i.e., "trace") amounts or concentrations, relative to the amounts or concentrations of other moieties or components present in the culture medium. In the present invention, these terms encompass $Ag^+$, $Al^{3+}$, $Ba^{2+}$, $Cd^{2+}$, $Co^{2+}$, $Cr^{3+}$, $CuI^+$, $Cu^{2+}$, $Fe^{2+}$, $Fe^{3+}$, $Ge^{4+}$, $Se^{4+}$, $Br^-$, $I^-$, $Mn^{2+}$, $F^-$, $Si^{4+}$, $V^{5+}$, $Mo^{6+}$, $Ni^{2+}$, $Rb^+$, $Sn^{2+}$ and $Zr^{4+}$ and salts thereof. For example, the following salts can be used as trace elements in the culture medium of the invention: $AgNO_3$, $AlCl_3 \cdot 6H_2O$, $Ba(C_2H_3O_2)_2$, $CdSO_4 \cdot 8H_2O$, $CdCl_2$, $CoCl_2 \cdot 6H_2O$, $Cr_2(SO_4)_3 \cdot 1H_2O$, $CuCl_2$, $FeSO_4$, $GeO_2$, $Na_2SeO_3$, $H_2SeO_3$, $KBr$, $KI$, $MnCl_2 \cdot 4H_2O$, $NaF$, $Na_2SiO_3 \cdot 9H_2O$, $NaVO_3$, $(NH_4)_6Mo_7O_{24} \cdot 4H_2O$, $NiSO_4 \cdot 6H_2O$, $RbCl$, $SnCl_2$, $ZnCl_2$, and $ZrOCl_2 \cdot 8H_2O$.

The term "amino acid" refers to amino acids or their derivatives (e.g., amino acid analogs), as well as their D- and L-forms. Examples of such amino acids include, without limitation, glycine, L-alanine, L-asparagine, L-cysteine, L-aspartic acid, L-glutamic acid, L-phenylalanine, L-histidine, L-isoleucine, L-lysine, L-leucine, L-glutamine, L-arginine, L-methionine, L-proline, L-hydroxyproline, L-serine, L-threonine, L-tryptophan, L-tyrosine, and L-valine, N-acetyl cysteine.

The term "transfection" is used herein to mean the delivery of nucleic acid, protein, or other macromolecule to a target cell, such that the nucleic acid, protein, or other macromolecule is expressed or has a biological function in the cell.

A "reagent for the introduction of macromolecules" into cells or a "transfection reagent" is any material, formulation or composition known to those of skill in the art that facilitates the entry of a macromolecule into a cell. For example, see U.S. Pat. No. 5,279,833. In some embodiments, the reagent can be a "transfection reagent" and can be any compound and/or composition that increases the uptake of one or more nucleic acids into one or more target cells. A variety of transfection reagents are known to those skilled in the art.

II. Baculovirus Expression System

The present disclosure relates to, inter alia, a baculovirus expression system and various components thereof, which can be used to produce baculovirus or protein. In some embodiments, a baculovirus expression system comprises:
  (a) a chemically-defined, yeast hydrolysate-free medium; and
  (b) a plurality of Sf9 cells.

In some embodiments, the baculovirus expression system further comprises a protein expression enhancer. In some embodiments, the protein expression enhancer comprises a histone deacetylase (HDAC) inhibitor. In some embodiments, the HDAC inhibitor is selected from apicidin, belinostat, CI-994, CRA-024781, curcumin, panobinostat, sodium butyrate, sodium phenylbutyrate, suberoylanilide hydroxamic acid, trichostatin A, and valproic acid. In some embodiments, the HDAC inhibitor is sodium butyrate, sodium phenylbutyrate, trichostatin A, or valproic acid.

In some embodiments, the baculovirus expression system further comprises a transfection reagent. Suitable transfection reagents can include, but are not limited to, one or more compounds and/or compositions comprising cationic polymers such as polyethyleneimine (PEI), polymers of positively charged amino acids such as polylysine and polyarginine, positively charged dendrimers and fractured dendrimers, cationic B-cyclodextrin containing polymers (CD-polymers), DEAE-dextran and the like. In some embodiments, a reagent for the introduction of macromolecules into cells can comprise one or more lipids which can be cationic lipids and/or neutral lipids. Preferred lipids include, but are not limited to, N-[1-(2,3-dioleyloxy) propyl]-N,N,N-trimethylamonium chloride (DOTMA), dioleoylphosphatidylcholine (DOPE), 1,2-Bis(oleoyloxy)-3-(4'-trimethylammonio) propane (DOTAP), dihydroxyl-dimyristylspermine tetrahydrochloride (DHDMS), hydroxyl-dimyristylspermine tetrahydrochloride (HDMS), 1,2-dioleoyl-3-(4'-trimethylammonio) butanoyl-sn-glycerol (DOTB), 1,2-dioleoyl-3-succinyl-sn-glycerol choline ester (DOSC), cholesteryl(4'-trimethylammonio)butanoate (ChoTB), cetyltrimethylammonium bromide (CTAB), 1,2-dioleoyl-3-dimethyl-hydroxyethyl ammonium bromide (DORI), 1,2-dioleyloxypropyl-3-dimethyl-hydroxyethyl ammonium bromide (DOME), 1,2-dimyristyloxypropyl-3-dimethylhydroxyethyl ammonium bromide (DMRIE), O,O'-didodecyl-N-[p(2-trimethylammonioethyloxy)benzoyl]-N,N,N-trimethylammonium chloride, spermine conjugated to one or more lipids (for example, 5-carboxyspermylglycine dioctadecylamide (DOGS), $N,N^I,N^{II},N^{III}$-tetramethyl-$N,N^I$, $N^{II},N^{III}$-tet-rapalmitylspermine (TM-TPS) and dipalmitoyl-phosphatidylethanolamine 5-carboxyspermylaminde (DPPES)), lipopolylysine (polylysine conjugated to DOPE), TRIS (Tris(hydroxymethyl)aminomethane, tromethamine) conjugated fatty acids (TFAs) and/or peptides such as trilysyl-alanyl-TRIS mono-, di-, and tri-palmitate, (3B-[N—(N', N'-dimethylaminoethane)-carbamoyl]cholesterol (DCChol), N-(α-trimethylammonioacetyl)-didodecyl-D-glutamate chloride (TMAG), dimethyl dioctadecylammonium bromide (DDAB), 2,3-dioleyloxy-N-[2(spermine-carboxamido) ethyl]-N,N-dimethyl-1-propanamin-iniumtrinuoroacetate (DOSPA) and combinations thereof.

Those skilled in the art will appreciate that certain combinations of the above mentioned lipids have been shown to be particularly suited for the introduction of nucleic acids into cells for example a 3:1 (w/w) combination of DOSPA and DOPE is available from Life Technologies Corporation, Carlsbad, Calif. under the trade name LIPOFECTAMINE™, a 1:1 (w/w) combination of DOTMA and DOPE is available from ThermoFisher Scientific under the trade name LIPOFECTIN®, a 1:1 (M/M) combination of DIVIRIE and cholesterol is available from Life Technologies Corporation, Carlsbad, Calif. under the trade name DIVIRIE-C reagent; a 1:1.5 (M/M) combination of TM-TPS and DOPE is available from Life Tech. In some embodiments, the transfection reagent is a cationic lipid transfection reagent. In some embodiments, the transfection reagent is a polymer-based transfection reagent. Other commercially available cationic lipid transfection reagents include, without limitation, TRANSFAST™ (available from Promega Corporation); LYOVEC™ (available from InvivoGen); DOTAP liposomal transfection reagent (available from Roche); TRANSIT® transfection reagents (available from Mirus); and Insect GENEJUICE® Transfection Reagent (EMD Millipore). Polymer-based transfection reagents include, without limitation, TURBOFECT™ transfection reagents (available from ThermoFisher Scientific); Xfect transfection reagent (available from Takara Bio USA); XTREMEGENE™ transfection reagents (available from Roche); Sigma Universal Transfection Reagent (available from Sigma-Aldrich); POLYMER In Vivo Transfection Reagent (available from Altogen Biosystems); and polyethylenimine (PEI). Additional transfection reagents that may be used herein include, without limitation, VIAFECT™ Transfection Reagent, FUGENE® 6 Transfection Reagent, and FUGENE® HD Transfection Reagent, each of which is available from Promega Corporation; and TRANSFECTIN™ Lipid Reagent, available from BioRad Laboratories, Inc.

In some embodiments, the medium is an insect cell medium. In embodiments, the insect cell medium is EXPISF™ CD Media, available from ThermoFisher Scientific. In embodiments, the insect cell medium is Grace's insect media, SF-900™ II, or SF-900™ III, each of which is available from ThermoFisher Scientific.

The original Sf9 cells were cloned from the parental IPLBSF-21 (Sf21) cell line that was derived from the pupal ovarian tissue of the fall army worm, *Spodoptera frugiperda*. Sf9 cells have been used extensively in research and development of viruses, in particular baculovirus. In some embodiments, the Sf9 cells described herein are Sf9 cells that have been adapted for growth in the chemically-defined, yeast lysate-free medium, for example by culturing/subculturing the cells for a period of time (e.g., at least 4, 6, 8, 10, 12, 15, 20 passages) in the medium. In some embodiments, the Sf9 cells are EXPISF9™ cells, available from ThermoFisher Scientific. In some embodiments, the Sf9 cells are GIBCO® Sf9 cells, available from ThermoFisher Scientific.

In some embodiments, the plurality of Sf9 cells are capable of growing in suspension culture in the medium. In some embodiments, the plurality of Sf9 cells are capable of growing in adherent culture in the medium.

In some embodiments, the plurality of Sf9 cells are capable of high-density growth when cultured in a chemically-defined, yeast lysate-free medium as described herein. In some embodiments, the plurality of Sf9 cells are adapted for high-density growth when cultured in a chemically-defined, yeast lysate-free medium as described herein. In some embodiments, the Sf9 cells are capable of peak cell density of about $1 \times 10^6$ cells per milliliter (cells/mL) to about $2 \times 10^8$ cells/mL. In some embodiments, the Sf9 cells are capable of peak cell density of about $2 \times 10^6$ cells/mL to about $2 \times 10^8$ cells/mL. In some embodiments, the Sf9 cells are capable of peak cell density of about $5 \times 10^6$ cells/mL to about $5 \times 10^7$ cells/mL. In some embodiments, the Sf9 cells are capable of peak cell density of about $5 \times 10^6$ cells/mL to about $4 \times 10^7$ cells/mL. In some embodiments, the Sf9 cells are capable of peak cell density of about $5 \times 10^6$ cells/mL to about $3 \times 10^7$ cells/mL. In some embodiments, the Sf9 cells are capable of peak cell density of about $6 \times 10^6$ cells/mL to about $3 \times 10^7$ cells/mL. In some embodiments, the Sf9 cells are capable of peak cell density of about $7 \times 10^6$ cells/mL to about $3 \times 10^7$ cells/mL. In some embodiments, the Sf9 cells are capable of peak cell density of about $8 \times 10^6$ cells/mL to about $3 \times 10^7$ cells/mL. In some embodiments, the Sf9 cells are capable of peak cell density of about $9 \times 10^6$ cells/mL to about $3 \times 10^7$ cells/mL. In some embodiments, the Sf9 cells are capable of peak cell density of about $1 \times 10^7$ cells/mL to about $3 \times 10^7$ cells/mL. In some embodiments, the Sf9 cells are capable of peak cell density of about $1 \times 10^7$ cells/mL to about $2.5 \times 10^7$ cells/mL. In some embodiments, the Sf9 cells are capable of peak cell density of about $2 \times 10^7$ cells/mL to about $2.5 \times 10^7$ cells/mL. In some embodiments, the Sf9 cells are capable of peak cell density of up to about $2.2 \times 10^7$ cells/mL. In some embodiments, the Sf9 cells are capable of peak cell density of about $1 \times 10^6$ cells/mL to about $5 \times 10^6$ cells/mL, about $5 \times 10^6$ cells/mL to about $1 \times 10^7$ cells/mL, about $1 \times 10^7$ cells/mL to about $5 \times 10^7$ cells/mL, about $5 \times 10^7$ cells/mL to about $1 \times 10^8$ cells/mL, or about $1 \times 10^8$ cells/mL to about $2 \times 10^8$ cells/mL.

In some embodiments, the cells are grown in a suspension culture. This includes a cell culture in which the majority or all of the cells in a culture vessel are present in suspension, and the minority or none of the cells in the culture vessel are attached to the vessel surface or to another surface within the vessel. In some embodiments, suspension culture has ≥ about 75% of the cells in the culture vessel are in suspension, not attached to a surface on or in the culture vessel. In some embodiments, a suspension culture has ≥ about 85% of the cells in the culture vessel are present in suspension, not attached to a surface on or in the culture vessel. In some embodiments, suspension culture has ≥ about 95% of the cells in the culture vessel present in suspension, not attached to a surface on or in the culture vessel.

In some embodiments, the baculovirus expression system further comprises instructions for using the system to express baculovirus. In some embodiments, the baculovirus expression system further comprises instructions for using the system to express protein from a baculovirus.

In some embodiments, the baculovirus expression system further comprises a baculovirus vector. In some embodiments, the baculovirus vector is a bacmid.

In some embodiments, the baculovirus expression system further comprises one or more components for making a recombinant baculovirus.

II. Insect Cell Medium

In some aspects, this disclosure relates to a medium for growth of insect cells. In some embodiments, the baculovirus expression system comprises the medium. The disclosure relates, in part, to a medium for insect cell culture comprising an inorganic salt selected from a barium salt, a cadmium salt, a copper salt, a magnesium salt, a manganese salt, a nickel salt, a potassium salt, a calcium salt, a silver salt, a tin salt, a zirconium salt, a sodium salt, or combinations thereof, and a vitamin. In some embodiments, the amount of inorganic salt is sufficient to support growth of insect cells. In some embodiments, the medium is a chemically-defined and yeast hydrolysate-free medium. In some embodiments, the medium does not comprise protein. In some embodiments, the medium does not comprise serum. In some embodiments, the medium does not comprise an ingredient derived from an animal.

In some embodiments, the medium comprises an organic or inorganic salt selected from an aluminum salt, a barium salt, a cadmium salt, a copper salt, a magnesium salt, a manganese salt, a nickel salt, a potassium salt, a calcium salt, a silver salt, a tin salt, a zirconium salt, a sodium salt, or combinations thereof. Salts include those made with organic or inorganic anions including, without limitation: $AgNO_3$, $AlCl_3 \cdot 6H_2O$, $Ba(C_2H_3O_2)_2$, $CaCl_2$, $CdSO_4 \cdot 8H_2O$, $COCl_2 \cdot 6H_2O$, $Cr_2(SO_4)_3 \cdot 1H_2O$, $CuCl_2$, $FeSO_4$, $FeCl_2$, $FeCl_3$, $Fe(NO_3)_3$, $GeO_2$, $Na_2SeO_3$, $H_2SeO_3$, $KBr$, $KCl$, $KI$, $MgCl_2$, $MgSO_4$, $MnCl_2 \cdot 4H_2O$, $NaF$, $Na_2SiO_3 \cdot 9H_2O$, $NaVO_3$, $Na_3VO_4$, $(NH_4)_6Mo_7O_{24} \cdot 4H_2O$, $Na_2HPO_4$, $NaH_2PO_4$, $NaHCO_3$, $NiSO_4 \cdot 6H_2O$, $NiCl_2$, $Ni(NO_3)_2$, RbCl, $SnCl_2$, $ZnCl_2$, $ZnSO_4$, $ZrOCl_{12} \cdot 8H_2O$, EDTA tetrasodium, In embodiments, the medium comprises sodium vanadate ($NaVO_3$ or $Na_3VO_4$) in a range of about $1 \times 10^{-5}$ grams per liter (g/L) to about $5 \times 10^{-3}$ g/L. In embodiments, the medium comprises sodium vanadate (NaVO3 or Na3VO4) in a range of about $5 \times 10^{-5}$ g/L to about $5 \times 10^{-3}$ g/L, about $1 \times 10^{-4}$ g/L to about $5 \times 10^{-5}$ g/L, about $5 \times 10^{-4}$ g/L to about $5 \times 10^{-3}$ g/L, or about $1 \times 10^{-3}$ g/L to about $5 \times 10^{-3}$ g/L. In embodiments, the medium comprises sodium vanadate ($NaVO_3$ or $Na_3VO_4$) in a range of about $5 \times 10^{-5}$ g/L to about $1 \times 10^{-3}$ g/L, about $5 \times 10^{-5}$ g/L to about $5 \times 10^{-4}$ g/L, or about $5 \times 10^{-5}$ g/L to about $1 \times 10^{-4}$ g/L. In embodiments, the medium comprises sodium vanadate ($NaVO_3$ or $Na_3VO_4$) in a range of about $1 \times 10^{-5}$ g/L to about $5 \times 10^{-5}$ g/L, about $5 \times 10^{-5}$ g/L to about $1 \times 10^{-4}$ g/L, about $1 \times 10^{-4}$ g/L to about $5 \times 10^{-4}$ g/L, about $5 \times 10^{-4}$ g/L to about $1 \times 10^{-5}$ g/L, or $1 \times 10^{-5}$ g/L to about $5 \times 10^{-5}$ g/L.

In embodiments, the medium comprises sodium metasilicate in a range of about $1 \times 10^{-5}$ grams per liter (g/L) to about $5 \times 10^{-3}$ g/L. In embodiments, the medium comprises sodium metasilicate in a range of about $5 \times 10^{-5}$ g/L to about $5 \times 10^{-3}$ g/L, about $1 \times 10^{-4}$ g/L to about $5 \times 10^{-3}$ g/L, or about $5 \times 10^{-4}$ g/L to about $5 \times 10^{-3}$ g/L. In embodiments, the medium comprises sodium metasilicate in a range of about $5 \times 10^{-5}$ g/L to about $1 \times 10^{-3}$ g/L, about $5 \times 10^{-5}$ g/L to about $5 \times 10^{-4}$ g/L, or about $5 \times 10^{-5}$ g/L to about $1 \times 10^{-4}$ g/L. In embodiments, the medium comprises sodium metasilicate in a range of about $1 \times 10^{-5}$ g/L to about $5 \times 10^{-5}$ g/L, $5 \times 10^{-5}$ g/L to about $1 \times 10^{-4}$ g/L, about $1 \times 10^{-4}$ g/L to about $5 \times 10^{-4}$ g/L, $5 \times 10^{-4}$ g/L to about $1 \times 10^{-3}$ g/L, or $1 \times 10^{-3}$ g/L to about $5 \times 10^{-3}$ g/L.

In embodiments, the medium comprises ammonium molybdate in a range of about $1 \times 10^{-6}$ g/L to about $5 \times 10^{-4}$ g/L. In embodiments, the medium comprises ammonium molybdate in a range of about $1 \times 10^{-6}$ g/L to about $1 \times 10^{-4}$ g/L, about $1 \times 10^{-6}$ g/L to about $5 \times 10^{-5}$ g/L, or about $1 \times 10^{-6}$ g/L to about $1 \times 10^{-5}$ g/L. In embodiments, the medium comprises ammonium molybdate in a range of about $5 \times 10^{-6}$ g/L to about $5 \times 10^{-4}$ g/L, about $1 \times 10^{-5}$ g/L to about $5 \times 10^{-4}$ g/L, or about $5 \times 10^{-5}$ g/L to about $5 \times 10^{-4}$ g/L. In embodiments, the medium comprises ammonium molybdate in a range of about $1 \times 10^{-6}$ g/L to about $5 \times 10^{-6}$ g/L, about $5 \times 10^{-6}$ g/L to about $1 \times 10^{-5}$ g/L, about $1 \times 10^{-5}$ g/L to about $5 \times 10^{-5}$ g/L, about $5 \times 10^{-5}$ g/L to about $1 \times 10^{-4}$ g/L, or about $1 \times 10^{-4}$ g/L to about $5 \times 10^{-4}$ g/L.

In embodiments, the medium comprises cadmium chloride in a range of about $1 \times 10^{-8}$ g/L to about $5 \times 10^{-4}$ g/L. In embodiments, the medium comprises cadmium chloride in a range of about $5 \times 10^{-8}$ g/L to about $5 \times 10^{4}$ g/L, about $1 \times 10^{-7}$ g/L to about $5 \times 10^{-4}$ g/L, about $5 \times 10^{-7}$ g/L to about $5 \times 10^{-4}$ g/L, about $1 \times 10^{-6}$ g/L to about $5 \times 10^{-4}$ g/L, about $5 \times 10^{-6}$ g/L to about $5 \times 10^{-4}$ g/L, about $1 \times 10^{-5}$ g/L to about $5 \times 10^{-4}$ g/L, or about $5 \times 10^{-5}$ g/L to about $5 \times 10^{-4}$ g/L. In embodiments, the medium comprises cadmium chloride in a range of about $1 \times 10^{-8}$ g/L to about $1 \times 10^{-4}$ g/L, about $1 \times 10^{-8}$ g/L to about $5 \times 10^{-5}$ g/L, about $1 \times 10^{-8}$ g/L to about $1 \times 10^{-5}$ g/L, about $1 \times 10^{-8}$ g/L to about $1 \times 10^{-6}$ g/L, or about $1 \times 10^{-8}$ g/L to about $1 \times 10^{-7}$ g/L. In embodiments, the medium comprises cadmium chloride in a range of about $1 \times 10^{-8}$ g/L to about $5 \times 10^{-8}$ g/L, about $5 \times 10^{-8}$ g/L to about $1 \times 10^{-7}$ g/L, about $1 \times 10^{-6}$ g/L to about $5 \times 10^{-7}$ g/L, about $5 \times 10^{-7}$ g/L to about $1 \times 10^{-6}$ g/L, about $1 \times 10^{-6}$ g/L to about $5 \times 10^{-6}$ g/L, $5 \times 10^{-6}$ g/L to about $1 \times 10^{-5}$ g/L, about $1 \times 10^{-5}$ g/L to about $5 \times 10^{-5}$ g/L, about $5 \times 10^{-5}$ g/L to about $1 \times 10^{-4}$ g/L, or $1 \times 10^{-4}$ g/L to about $5 \times 10^{-4}$ g/L.

In embodiments, the medium comprises a zinc salt ($ZnCl_2$ and/or $ZnSO_4$) in a range of about $1 \times 10^{-4}$ g/L to about $5 \times 10^{-2}$ g/L. In embodiments, the medium comprises a zinc salt ($ZnCl_2$ and/or $ZnSO_4$) in a range of about $5 \times 10^{-4}$ g/L to about $5 \times 10^{-2}$ g/L, about $1 \times 10^{-3}$ g/L to about $5 \times 10^{-2}$ g/L, about $5 \times 10^{-3}$ g/L to about $5 \times 10^{-2}$ g/L, or about $1 \times 10^{-2}$ g/L to about $5 \times 10^{-2}$ g/L. In embodiments, the medium comprises a zinc salt ($ZnCl_2$ and/or $ZnSO_4$) in a range of about $5 \times 10^{-4}$ g/L to about $1 \times 10^{-2}$ g/L, about $5 \times 10^{-4}$ g/L to about $5 \times 10^{-3}$ g/L, or about $5 \times 10^{-4}$ g/L to about $1 \times 10^{-3}$ g/L. In embodiments, the medium comprises a zinc salt ($ZnCl_2$ and/or $ZnSO_4$) in a range of about $1 \times 10^{-4}$ g/L to about $5 \times 10^{-4}$ g/L, about $5 \times 10^{-4}$ g/L to about $1 \times 10^{-3}$ g/L, about $1 \times 10^{-3}$ g/L to about $5 \times 10^{-3}$ g/L, about $5 \times 10^{-3}$ g/L to about $1 \times 10^{-2}$ g/L, or about $1 \times 10^{-2}$ g/L to about $5 \times 10^{-2}$ g/L.

In embodiments, the medium comprises an iron salt (e.g., $FeSO_4$, $FeCl_2$, $FeCl_3$, and/or $Fe(NO_3)_3$) in a range of about $1 \times 10^{-4}$ g/L to about $5 \times 10^{-2}$ g/L. In embodiments, the medium comprises an iron salt (e.g., $FeSO_4$, $FeCl_2$, $FeCl_3$, and/or $Fe(NO_3)_3$) in a range of about $5 \times 10^{-4}$ g/L to about $5 \times 10^{-2}$ g/L, about $1 \times 10^{-3}$ g/L to about $5 \times 10^{-2}$ g/L, about $5 \times 10^{-9}$ g/L to about $5 \times 10^{-2}$ g/L, or about $1 \times 10^{-2}$ g/L to about $5 \times 10^{-2}$ g/L. In embodiments, the medium comprises an iron salt (e.g., $FeSO_4$, $FeCl_2$, $FeCl_3$, and/or $Fe(NO_3)_3$) in a range of about $5 \times 10^{-4}$ g/L to about $1 \times 10^{-2}$ g/L, about $5 \times 10^{-4}$ g/L to about $5 \times 10^{-3}$ g/L, or about $5 \times 10^{-4}$ g/L to about $1 \times 10^{-3}$ g/L. In embodiments, the medium comprises an iron salt (e.g., $FeSO_4$, $FeCl_2$, $FeCl_3$, and/or $Fe(NO_3)_3$) in a range of about $1 \times 10^{-4}$ g/L to about $5 \times 10^{-4}$ g/L, $5 \times 10^{-4}$ g/L to about $1 \times 10^{-3}$ g/L, $1 \times 10^{-3}$ g/L to about $5 \times 10^{-3}$ g/L, $5 \times 10^{-3}$ g/L to about $1 \times 10^{-2}$ g/L, or $1 \times 10^{-2}$ g/L to about $5 \times 10^{-2}$ g/L.

In embodiments, the medium comprises a potassium salt (e.g., KBr, KCl, and/or KI) in a range of about $1 \times 10^{-9}$ g/L to about $5 \times 10^{-7}$ g/L. In embodiments, the medium comprises a potassium salt (e.g., KBr, KCl, and/or KI) in a range of about $5 \times 10^{-9}$ g/L to about $5 \times 10^{-7}$ g/L, about $1 \times 10^{-7}$ g/L to about $5 \times 10^{-7}$ g/L, about $5 \times 10^{-7}$ g/L to about $5 \times 10^{-7}$ g/L, or about $1 \times 10^{-7}$ g/L to about $5 \times 10^{-7}$ g/L. In embodiments, the medium comprises a potassium salt (e.g., KBr, KCl, and/or KI) in a range of about $5 \times 10^{-9}$ g/L to about $1 \times 10^{-7}$ g/L, about $5 \times 10^{-9}$ g/L to about $5 \times 10^{-8}$ g/L, or about $5 \times 10^{-9}$ g/L to about $1 \times 10^{-8}$ g/L. In embodiments, the medium comprises a potassium salt (e.g., KBr, KCl, and/or KI) in a range of about $1 \times 10^{-9}$ g/L to about $5 \times 10^{-9}$ g/L, about $5 \times 10^{-9}$ g/L to about $1 \times 10^{-8}$ g/L, about $1 \times 10^{-8}$ g/L to about $5 \times 10^{-8}$ g/L, about $5 \times 10^{-8}$ g/L to about $1 \times 10^{-7}$ g/L, or about $1 \times 10^{-7}$ g/L to about $5 \times 10^{-7}$ g/L.

In embodiments, the medium comprises a silver salt (e.g., $AgNO_3$) in a range of about $1 \times 10^{-9}$ g/L to about $5 \times 10^{-7}$ g/L. In embodiments, the medium comprises a silver salt (e.g., $AgNO_3$) in a range of about $5 \times 10^{-9}$ g/L to about $5 \times 10$-7 g/L, about $1 \times 10^{-8}$ g/L to about $5 \times 10^{-7}$ g/L, about $5 \times 10^{-7}$ g/L to about $5 \times 10^{-7}$ g/L, or about $1 \times 10^{-7}$ g/L to about $5 \times 10^{-7}$ g/L. In embodiments, the medium comprises a silver salt (e.g., $AgNO_3$) in a range of about $5 \times 10^{-9}$ g/L to about $1 \times 10^{-7}$ g/L, about $5 \times 10^{-9}$ g/L to about $5 \times 10^{-8}$ g/L, or about $5 \times 10^{-9}$ g/L to about $1 \times 10^{-8}$ g/L. In embodiments, the medium comprises a silver salt (e.g., $AgNO_3$) in a range of about $1 \times 10^{-9}$ g/L to about $5 \times 10^{-9}$ g/L, about $5 \times 10^{-9}$ g/L to about $1 \times 10^{-8}$ g/L, about $1 \times 10^{-8}$ g/L to about $5 \times 10^{-8}$ g/L, about $5 \times 10^{-8}$ g/L to about $1 \times 10^{-7}$ g/L, or about $1 \times 10^{-7}$ g/L to about $5 \times 10^{-7}$ g/L.

In embodiments, the medium comprises stannous chloride in a range of about $1 \times 10^{-9}$ g/L to about $5 \times 10^{-7}$ g/L. In embodiments, the medium comprises stannous chloride in a range of about $5 \times 10^{-9}$ g/L to about $5 \times 10^{-7}$ g/L, about $1 \times 10^{-8}$ g/L to about $5 \times 10^{-7}$ g/L, about $5 \times 10^{-8}$ g/L to about $5 \times 10^{-7}$ g/L, or about $1 \times 10^{-7}$ g/L to about $5 \times 10^{-7}$ g/L. In embodiments, the medium comprises stannous chloride in a range of about $5 \times 10^{-9}$ g/L to about $1 \times 10^{-7}$ g/L, about $5 \times 10^{-9}$ g/L to about $5 \times 10^{-8}$ g/L, or about $5 \times 10^{9}$ g/L to about $1 \times 10^{-8}$ g/L. In embodiments, the medium comprises stannous chloride in a range of about $1 \times 10^{-9}$ g/L to about $5 \times 10^{-9}$ g/L, about $5 \times 10^{-9}$ g/L to about $1 \times 10^{-8}$ g/L, about $1 \times 10^{-8}$ g/L to about $5 \times 10^{-8}$ g/L, about $5 \times 10^{-8}$ g/L to about $1 \times 10^{-7}$ g/L, or about $1 \times 10^{-7}$ g/L to about $5 \times 10^{-7}$ g/L.

In embodiments, the medium comprises a nickel salt (e.g., $NiSO_4$, $NiCl_2$, and/or $Ni(NO_3)_2$) in a range of about $1 \times 10^{-5}$ g/L to about $5 \times 10^{-7}$ g/L. In embodiments, the medium comprises a nickel salt (e.g., $NiSO_4$, $NiCl_2$, and/or $Ni(NO_3)_2$) in a range of about $5 \times 10^{9}$ g/L to about $5 \times 10^{-7}$ g/L, about $1 \times 10^{-8}$ g/L to about $5 \times 10^{-7}$ g/L, about $5 \times 10^{-8}$ g/L to about $5 \times 10^{-7}$ g/L, or about $1 \times 10^{-7}$ g/L to about $5 \times 10^{7}$ g/L. In embodiments, the medium comprises a nickel salt (e.g., $NiSO_4$, $NiCl_2$, and/or $Ni(NO_3)_2$) in a range of about $5 \times 10^{-9}$ g/L to about $1 \times 10^{-7}$ g/L, about $5 \times 10^{-9}$ g/L to about $5 \times 10^{-8}$ g/L, or about $5 \times 10^{-9}$ g/L to about $1 \times 10^{-8}$ g/L.

In embodiments, the medium comprises a nickel salt (e.g., $NiSO_4$, $NiCl_2$, and/or $Ni(NO_3)_2$) in a range of about $1 \times 10^{-9}$ g/L to about $5 \times 10^{9}$ g/L, about $5 \times 10^{-9}$ g/L to about $1 \times 10^{-8}$ g/L, about $1 \times 10^{-8}$ g/L to about $5 \times 10^{-8}$ g/L, about $5 \times 10^{-8}$ g/L to about $1 \times 10^{-7}$ g/L, or about $1 \times 10^{-7}$ g/L to about $5 \times 10^{-7}$ g/L.

In embodiments, the medium comprises $ZrOCl_2$ in a range of about $1 \times 10^{-5}$ g/L to about $5 \times 10^{-6}$ g/L. In embodiments, the medium comprises $ZrOCl_2$ in a range of about $5 \times 10^{9}$ g/L to about $5 \times 10^{-6}$ g/L, about $1 \times 10^{-8}$ g/L to about $5 \times 10^{-6}$ g/L, about $5 \times 10^{-8}$ g/L to about $5 \times 10^{-6}$ g/L, about $1 \times 10^{-7}$ g/L to about $5 \times 10^{-6}$ g/L, or about $5 \times 10^{-7}$ g/L to about $5 \times 10^{-6}$ g/L. In embodiments, the medium comprises $ZrOCl_2$ in a range of about $1 \times 10^{-9}$ g/L to about $1 \times 10^{-6}$ g/L, about $1 \times 10^{-9}$ g/L to about $5 \times 10^{-7}$ g/L, about $1 \times 10^{-9}$ g/L to about $1 \times 10^{-7}$ g/L, about $1 \times 10^{-9}$ g/L to about $1 \times 10^{-8}$ g/L. In embodiments, the medium comprises $ZrOCl_2$ in a range of about $1 \times 10^{-9}$ g/L to about $5 \times 10^{-9}$ g/L, about $5 \times 10^{-9}$ g/L to about $1 \times 10^{-8}$ g/L, about $1 \times 10^{-8}$ g/L to about $5 \times 10^{-8}$ g/L, $5 \times 10^{-8}$ g/L to about $1 \times 10^{-7}$ g/L, $1 \times 10^{-7}$ g/L to about $5 \times 10^{-7}$ g/L, $5 \times 10^{-7}$ g/L to about $1 \times 10^{-6}$ g/L, or $1 \times 10^{-6}$ g/L to about $5 \times 10^{-6}$ g/L.

In embodiments, the medium comprises sodium fluoride in a range of about $1 \times 10^{-9}$ g/L to about $5 \times 10^{-6}$ g/L. In embodiments, the medium comprises sodium fluoride in a range of about $5 \times 10^{9}$ g/L to about $5 \times 10^{-6}$ g/L, about $1 \times 10^{-8}$ g/L to about $5 \times 10^{-6}$ g/L, about $5 \times 10.8$ g/L to about $5 \times 10^{-6}$ g/L, about $1 \times 10^{-7}$ g/L to about $5 \times 10^{-6}$ g/L, or about $5 \times 10^{-7}$ g/L to about $5 \times 10^{-6}$ g/L. In embodiments, the medium comprises sodium fluoride in a range of about $1 \times 10^{-9}$ g/L to about $1 \times 10^{-6}$ g/L, about $1 \times 10^{-9}$ g/L to about $5 \times 10^{-7}$ g/L, about $1 \times 10^{-9}$ g/L to about $1 \times 10^{-7}$ g/L, about $1 \times 10^{-9}$ g/L to about $1 \times 10^{-8}$ g/L. In embodiments, the medium comprises sodium fluoride in a range of about $1 \times 10^{9}$ g/L to about $5 \times 10^{9}$ g/L, about $5 \times 10^{-9}$ g/L to about $1 \times 10^{-8}$ g/L, about $1 \times 10^{-8}$ g/L to about $5 \times 10^{-8}$ g/L, about $5 \times 10^{-8}$ g/L to about $1 \times 10^{-7}$ g/L, about $1 \times 10^{-7}$ g/L to about $5 \times 10^{-7}$ g/L, about $5 \times 10^{-7}$ g/L to about $1 \times 10^{-6}$ g/L, or about $1 \times 10^{-6}$ g/L to about $5 \times 10^{-6}$ g/L.

In embodiments, the medium comprises barium acetate in a range of about $1 \times 10^{-9}$ g/L to about $5 \times 10^{-6}$ g/L. In embodiments, the medium comprises barium acetate in a range of about $5 \times 10^{-9}$ g/L to about $5 \times 10^{-6}$ g/L, about $1 \times 10^{-8}$ g/L to about $5 \times 10^{-6}$ g/L, about $5 \times 10^{-8}$ g/L to about $5 \times 10^{-6}$ g/L, about $1 \times 10^{-7}$ g/L to about $5 \times 10^{-6}$ g/L, or about $5 \times 10^{-7}$ g/L to about $5 \times 10^{-6}$ g/L. In embodiments, the medium comprises barium acetate in a range of about $1 \times 10^{-5}$ g/L to about $1 \times 10^{-6}$ g/L, about $1 \times 10^{-5}$ g/L to about $5 \times 10^{-7}$ g/L, about $1 \times 10^{-9}$ g/L to about $1 \times 10^{-7}$ g/L, about $1 \times 10^{-9}$ g/L to about $1 \times 10^{-8}$ g/L. In embodiments, the medium comprises barium acetate in a range of about $1 \times 10^{-9}$ g/L to about $5 \times 10^{-9}$ g/L, about $5 \times 10^{-9}$ g/L to about $1 \times 10^{-8}$ g/L, about $1 \times 10^{-8}$ g/L to about $5 \times 10^{-8}$ g/L, about $5 \times 10^{-8}$ g/L to about $1 \times 10^{-7}$ g/L, about $1 \times 10^{-7}$ g/L to about $5 \times 10^{-7}$ g/L, about $5 \times 10^{-7}$ g/L to about $1 \times 10^{-6}$ g/L, or about $1 \times 10^{-6}$ g/L to about $5 \times 10^{-6}$ g/L.

In embodiments, the medium comprises a magnesium salt (e.g., $MgCl_2$ and/or $MgSO_4$) in a range of about 0.01 g/L to about 10 g/L. In embodiments, the medium comprises a magnesium salt (e.g., $MgCl_2$ and/or $MgSO_4$) in a range of about 0.05 g/L to about 10 g/L, about 0.1 g/L to about 10 g/L, about 0.5 g/L to about 10 g/L, or about 1 g/L to about 10 g/L. In embodiments, the medium comprises a magnesium salt (e.g., $MgCl_2$ and/or $MgSO_4$) in a range of about 0.01 g/L to about 5 g/L, about 0.01 g/L to about 1 g/L, about 0.01 g/L to about 0.5 g/L, or about 0.01 g/L to about 0.1 g/L. In embodiments, the medium comprises a magnesium salt (e.g., $MgCl_2$ and/or $MgSO_4$) in a range of about 0.01 g/L to about 0.05 g/L, about 0.05 g/L to about 0.1 g/L, about 0.1 g/L to about 0.5 g/L, about 0.5 g/L to about 1 g/L, about 1 g/L to about 5 g/L, or about 5 g/L to about 10 g/L.

In some embodiments, the medium comprises a vitamin selected from para-aminobenzoic acid, vitamin B12, biotin, choline (e.g., choline chloride), folic acid, inositol, nicotinic acid, niacinamide, pantothenic acid, pyridoxine, riboflavin, thiamine, or combinations thereof. Each vitamin may be present in the medium in a range of about $1 \times 10^{-4}$ g/L to about 0.5 g/L. In embodiments, the medium comprises the vitamin in a range of about $5 \times 10^{-4}$ g/L to about 0.5 g/L, about $1 \times 10^{-7}$ g/L to about 0.5 g/L, about $5 \times 10^{-3}$ g/L to about 0.5 g/L, about 0.01 g/L to about 0.5 g/L, or about 0.05 g/L to about 0.5 g/L. In embodiments, the medium comprises the vitamin in a range of about $1 \times 10^{-4}$ g/L to about 0.1 g/L, about $1 \times 10^{-4}$ g/L to about 0.05 g/L, about $1 \times 10^{-4}$ g/L to about 0.01 g/L, about $1 \times 10^{-4}$ g/L to about $5 \times 10^{-3}$ g/L, or about $1 \times 10^{-4}$ g/L to about $1 \times 10^{-3}$ g/L. In embodiments, the medium comprises the vitamin in a range of about $1 \times 10^{-4}$ g/L to about $5 \times 10^{-4}$ g/L, about $5 \times 10^{-5}$ g/L to about $1 \times 10^{-3}$, about $1 \times 10^{-3}$ g/L to about $5 \times 10^{-3}$ g/L, about $5 \times 10^{-3}$ g/L to about 0.01 g/L, about 0.01 g/L to about 0.05 g/L, about 0.05 g/L to about 0.1 g/L, or 0.1 g/L to about 0.5 g/L.

In some embodiments, the medium comprises a fatty acid (or ester thereof, e.g. a fatty acid methyl ester thereof) selected from methyl meristate, tocopherol, methyl lioleate, methyl oleate, methyl arachidonate, methyl linolenate, methyl palmitoleate, methyl palmitate, and combinations thereof. Each fatty acid and/or fatty acid methyl ester may be present in the medium in a range of about $1 \times 10^{-5}$ g/L to about $1 \times 10^{-2}$ g/L. In embodiments, the medium comprises the fatty acid (or ester thereof) in a range of about $5 \times 10^{-5}$ g/L to about $1 \times 10^{-2}$ g/L, about $1 \times 10^{-4}$ g/L to about $1 \times 10^{-2}$ g/L, about $5 \times 10^{-4}$ g/L to about $1 \times 10^{-5}$ g/L, or about $1 \times 10^{-3}$ g/L to about $1 \times 10^{-2}$ g/L. In embodiments, the medium comprises the fatty acid (or ester thereof) in a range of about $1 \times 10^{-5}$ g/L to about $5 \times 10^{-5}$ g/L, about $1 \times 10^{-5}$ g/L to about $1 \times 10^{-3}$ g/L, about $1 \times 10^{-5}$ g/L to about $5 \times 10^{-4}$ g/L, or about $1 \times 10^{-5}$ g/L to about $1 \times 10^{-4}$ g/L. In embodiments, the medium comprises the fatty acid (or ester thereof) in a range of about $1 \times 10^{-5}$ g/L to about $5 \times 10^{-5}$ g/L, $5 \times 10^{-5}$ g/L to about $1 \times 10^{-4}$ g/L, $1 \times 10^{-4}$ g/L to about $5 \times 10^{-4}$ g/L, $5 \times 10^{-4}$ g/L to about $1 \times 10^{-3}$ g/L, $1 \times 10^{-3}$ g/L to about $5 \times 10^{-3}$ g/L, or $5 \times 10^{3}$ g/L to about $1 \times 10^{-2}$ g/L.

In some embodiments, the medium comprises an energy source selected from glucose, sucrose, pyruvate (e.g., sodium pyruvate), maltose, trehalose, or combinations thereof. In embodiments, the medium comprises the energy source in a range between about 0.01 g/L and about 30 g/L. In embodiments, the medium comprises the energy source in a range between about 0.05 g/L and about 30 g/L, about 0.1 g/L and about 30 g/L, about 0.5 g/L and about 30 g/L, about 1 g/L and about 30 g/L, about 5 g/L and about 30 g/L, about 10 g/L and about 30 g/l, or about 20 g/L and about 30 g/L. In embodiments, the medium comprises the energy source in a range between about 0.01 g/L and about 20 g/L, about 0.01 g/L and about 10 g/L, about 0.01 g/L and about 5 g/L, about 0.01 g/L and about 1 g/L, about 0.01 g/L and about 0.5 g/L, or about 0.01 g/L and about 0.1 g/L. In embodiments, the medium comprises the energy source in a range between about 0.01 g/L and about 0.05 g/L, about 0.05 g/L and about 0.1 g/L, about 0.1 g/L and about 0.5 g/L, about 0.5 g/L and about 1 g/L, about 1 g/L and about 5 g/L, about 5 g/L and about 10 g/L, or about 10 g/L and about 20 g/L.

In some embodiments, the medium comprises an additional ingredient selected from an emulsifier, a surfactant, an antioxidant, a buffer, a poloxamer, a metal binding compound, or combinations thereof. In some embodiments, the medium comprises an additional ingredient selected from polysorbate, ethanolamine, putrescine, spermine, sperimidine, a hydroxypyridine derivative (e.g., 2-hydroxypyridine-N-oxide, 3-hydroxy-4-pyrone, 3-hydroxypypyrid-2-one, 1-methyl-3-hydroxypyrid-2-one, or 2-hydroxy-nicotinic acid), EDTA, 2-mercaptoethanol, B-glycerophosphate, and cholesterol. Each additional ingredient may be present in the medium in any amount, for example between about $1 \times 10^{-4}$ g/L and about 10 g/L. In embodiments, the medium comprises the additional ingredient in a range between about $5 \times 10^{-4}$ g/L and about 10 g/L, about $1 \times 10^{-3}$ g/L and about 10 g/L, about $5 \times 10^{3}$ g/L and about 10 g/L, about $1 \times 10^{-2}$ g/L and about 10 g/L, about $5 \times 10^{-5}$ g/L and about 10 g/L, about 0.1 g/L and about 10 g/L, about 0.5 and about 10 g/L, and about 1 and about 10 g/L. In embodiments, the medium comprises the additional ingredient in a range between about $1 \times 10^{-4}$ g/L and about 5 g/L, about $1 \times 10^{-4}$ g/L and about 1 g/L, about $1 \times 10^{-4}$ g/L and about 0.5 g/L, about $1 \times 10^{-4}$ g/L and about 0.1 g/L, about $1 \times 10^{-4}$ g/L and about 0.05 g/L, about $1 \times 10^{-4}$ g/L and about 0.01 g/L, or about $1 \times 10^{-4}$ g/L and about $1 \times 10^{-3}$ g/L. In embodiments, the medium comprises the additional ingredient in a range between about $1 \times 10^{-4}$ g/L and about $5 \times 10^{-4}$ g/L, about $5 \times 10^{-4}$ g/L and about $1 \times 10^{-3}$ g/L, about $1 \times 10^{-3}$ g/L and about $5 \times 10^{-5}$ g/L, about $5 \times 10^{-5}$ g/L and about 0.01 g/L, about 0.01 g/L and about 0.05 g/L, about 0.05 g/L and about 0.1 g/L, about 0.1 g/L and about 0.5 g/L, about 0.5 g/L and about 1 g/L, about 1 g/L and about 5 g/L, or about 5 g/L and about 10 g/L.

In some embodiments, the medium comprises an amino acid selected from L-alanine, L-cysteine, L-aspartic acid, L-glutamic acid, L-phenylalanine, glycine, L-histidine, L-isoleucine, L-lysine, L-leucine, L-methionine, L-asparagine, pyrrolysine, L-proline, L-glutamine, L-arginine, L-serine, L-threonine, selenocysteine, L-valine, L-tryptophan, L-tyrosine, carnitine, levothyroxine, hydroxyproline, selenomethionine, taurine, citrulline, ornithine, or combinations thereof. In some embodiments, the amino acid is a stable analog of an amino acid (e.g., GLUTAMAX™, available from ThermoFisher Scientific). In embodiments, each amino acid may be present in the medium in a range of about 0.1 g/L and about 8 g/L.

IV. Methods of Use

The disclosure relates, in part, to a method of baculovirus production comprising:
(a) culturing insect cells in a chemically-defined, yeast hydrolysate-free medium;
(b) transfecting the cells with a bacmid; and
(c) harvesting the virus from the insect cell culture.

In some embodiments, the cells are transfected using a cationic lipid transfection reagent or a polymer-based transfection reagent.

In some embodiments, the insect cells are Sf9 cells. In some embodiments, the insect cells are in suspension culture. In some embodiments, the insect cells are in adherent (monolayer) culture.

In some embodiments, the transfection step is performed when the insect cells are present at a viable cell density between $1 \times 10^6$ cells/mL and $5 \times 10^7$ cells/mL, between about $1 \times 10^6$ cells/mL and $1 \times 10^7$ cells/mL, or between about $5 \times 10^6$ cells/mL and $1 \times 10^7$ cells/mL. In some embodiments, the transfection step is performed when the insect cells are ≥75% viable, ≥80% viable, ≥85% viable, ≥90% viable, or ≥95% viable.

In some embodiments, the medium is a medium as described herein.

In some embodiments, the medium is not replenished, replaced, or supplemented with additional or fresh medium after the transfection step.

In some embodiments, the harvested baculovirus has a titer of at least $5 \times 10^7$ infectious virus particles per milliliter (IVP/mL). In some embodiments, the harvested baculovirus has a titer of at least $1 \times 10^8$ IVP/mL. In some embodiments, the harvested baculovirus has a titer of between about $5 \times 10^7$ IVP/mL and about $1 \times 10^{10}$ IVP/mL, between about $5 \times 10^7$ IVP/mL and about $5 \times 10^9$ IVP/mL, between about $5 \times 10^7$ IVP/mL and about $1 \times 10^9$ IVP/mL, between about $1 \times 10^8$ IVP/mL and about $1 \times 10^{10}$ IVP/mL, between about $5 \times 10^8$ IVP/mL and about $1 \times 10^{10}$ IVP/mL, or between about $1 \times 10^7$ IVP/mL and about $1 \times 10^{10}$ IVP/mL. In some embodiments, the harvested baculovirus has a titer of between about $5 \times 10^7$ IVP/mL and about $1 \times 10^8$ IVP/mL, about $1 \times 10^8$ IVP/mL and about $5 \times 10^8$ IVP/mL, about $5 \times 10^8$ IVP/mL and about $1 \times 10^9$ IVP/mL, about $1 \times 10^9$ IVP/mL and about $5 \times 10^9$ IVP/mL, and about $5 \times 10^9$ IVP/mL and about $1 \times 10^{10}$ IVP/mL.

The disclosure relates, in part, to a method of protein production from a baculovirus comprising:
(a) culturing insect cells in a chemically-defined, yeast hydrolysate-free medium; and
(b) infecting the insect cells with a baculovirus that expresses the protein.

In some embodiments, the method further comprises: (c) culturing the infected cells for a period of time to produce the protein.

In some embodiments, the method further comprises: (d) harvesting the protein.

In some embodiments, steps (a) through (d) take between 5 days and 15 days. In some embodiments, the protein is harvested about 24 hours to about 120 hours after infection.

In some embodiments, a protein expression enhancer is added to the medium before step (b). In some embodiments, the protein expression enhancer is added at least 10 hours before infection. In some embodiments, the protein expression enhancer is added at least 12 hours, at least 15 hours, at least 18 hours, at least 21 hours, at least 24 hours, at least 27 hours, at least 30 hours, at least 33 hours, or at least 36 hours before infection. In some embodiments, the protein expression enhancer is added between 10 hours and 36 hours before infection. In some embodiments, the protein expression enhancer is added between 12 hours and 36 hours, between 15 hours and 36 hours, between 18 hours and 36 hours, between 21 hours and 36 hours, between 24 hours and 36 hours, between 27 hours and 36 hours, or between 30 hours and 36 hours before infection. In some embodiments, the protein expression enhancer is added between 10 hours and 33 hours, between 10 hours and 30 hours, between 10 hours and 27 hours, between 10 hours and 24 hours, between 10 hours and 21 hours, between 10 hours and 18 hours, or between 10 hours and 15 hours before infection.

In some embodiments, the protein expression enhancer comprises a histone deacetylase (HDAC) inhibitor. In some embodiments, the HDAC inhibitor is selected from apicidin, belinostat, CI-994, CRA-024781, curcumin, panobinostat, sodium butyrate, sodium phenylbutyrate, suberoylanilide hydroxamic acid, trichostatin A, and valproic acid. In some embodiments, the HDAC inhibitor is sodium butyrate, sodium phenylbutyrate, richostatin A, or valproic acid.

In some embodiments, the insect cells are Sf9 cells.

In some embodiments, the insect cells are capable of high-density growth in the medium. In some embodiments, the insect cells are capable of peak cell density of about $2\times10^6$ to about $2\times10^8$ cells per milliliter (cells/mL).

In some embodiments, the insect cells are in suspension culture. In some embodiments, the insect cells are in adherent culture.

In some embodiments, the infection step is performed when the insect cells are present at a viable cell density of between $1\times10^6$ cells/mL and $5\times10^7$ cells/mL, between about $1\times10^6$ cells/mL and $1\times10^7$ cells/mL, or between about $5\times10^6$ cells/mL and $1\times10^7$ cells/mL. In some embodiments, the infection step is performed when the insect cells are ≥75% viable, ≥80% viable, ≥85% viable, ≥90% viable, or ≥95% viable.

In some embodiments, the baculovirus used to infect the insect cells has a multiplicity of infection (MOI) between 1 and 10, 2 and 10, 3 and 10, 4 and 10, 5 and 10, 6 and 10, 7 and 10, or 8 and 10. In some embodiments, the baculovirus used to infect the insect cells has a multiplicity of infection (MOI) between 2 and 9, 3 and 8, or 4 and 7. In some embodiments, the baculovirus used to infect the insect cells has a MOI of about 5.

In some embodiments, the medium is not replaced, replenished, or supplemented with fresh medium during protein production.

In some embodiments, the insect cells are in adherent culture. In some embodiments, the insect cells are in suspension culture.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Sf9 Cell Culture

Sf9 cells were adapted to culture in chemically-defined, yeast lysate-free medium (hereinafter referred to as "the yeast lysate-free medium") by growth in the medium for multiple passages in shake flask culture.

Adapted Sf9 cells were incubated in the yeast lysate-free medium in a 27° C. non-humidified, air regulated non-$CO_2$ atmosphere on an orbital shaker platform. Cells were sub-cultured once cells reached a density of at least $5\times10^6$ viable cells per milliliter (VCM), and generally less than about $10\times10^6$ VCM. Cell viability was determined by trypan blue exclusion method or automated cell counter.

For long-term storage, adapted Sf9 cells were frozen in 92.5% conditioned yeast lysate-free medium with 7.5% dimethylsulfoxide (DMSO), using standard cryogenic procedures.

To determine adapted Sf9 cell viability in the yeast lysate-free medium versus standard insect cell medium containing yeast lysate, cells were grown in each medium and viable cell density determined over 10 days in culture. As shown in FIG. 1A, cells grown in the yeast lysate-free medium (heavy lines) achieved higher viable cell density over time (solid lines), and had greater viability after 6-10 days in culture (dashed lines), compared to cells grown in the standard insect cell medium (light lines).

Example 2: Baculovirus Generation—Transfection of Sf9 Cells

Bacmid DNA was produced using the BAC-TO-BAC™ Baculovirus Expression System (ThermoFisher Scientific). Sf9 cells that were adapted to culture in the yeast-lysate free medium were cultured in the yeast lysate-free medium as described in Example 1.

Adherent-Based Transfection

Adapted Sf9 cells were cultured until they reached a density of between about $5\times10^6$ and about $10\times10^6$ VCM and greater than or equal to 90% viability. Cells were seeded into 6-well plates at a final density of about $1\times10^6$ viable cells per well in a total volume of 3 mL yeast lysate-free medium per well. Cells were allowed to attach for 30 to 60 minutes in a 27° C. non-humidified, air regulated non-$CO_2$ atmosphere incubator.

Cells were transfected with cationic lipid transfection reagent at a ratio of about 1 µg DNA per 10 µL transfection reagent. Briefly, transfection reagent was diluted into OPTIMEM™ I Reduced Serum Medium (250 µL) and incubated for 5 minutes at room temperature. Bacmid DNA was added to the diluted transfection reagent, mixed, and incubated for 5 minutes at room temperature. The solution was transferred dropwise to the cells in the 6-well plate. The transfected cells were incubated for 72-96 hours.

Suspension-Based Transfection

Cells were cultured until they reached a density of between about $5\times10^6$ and about $10\times10^6$ VCM and greater than or equal to 90% viability. Cells were diluted to a final density of about $2.5\times10^6$ viable cells per mL in a total volume of 25 mL yeast lysate-free medium in a 125-mL non-baffled, vented shaker flask. Cells were allowed to recover for up to 30 minutes in a 27° C. non-humidified, air regulated non-$CO_2$ atmosphere incubator on an orbital shaker platform.

Cells were transfected with cationic lipid transfection reagent at a ratio of about 12.5 µg DNA per 30 µL transfection reagent. Briefly, transfection reagent was diluted into OPTIMEM™ I Reduced Serum Medium (1 mL) and incubated for 5 minutes at room temperature. Bacmid DNA was added to the diluted transfection reagent, mixed, and incubated for 5 minutes at room temperature. The solution was transferred dropwise to the cells in the shake flask. The transfected cells were incubated for 72-96 hours.

Example 3: Baculovirus Generation—Isolation of Viral Stock

When cells dropped to about 60% to 80% viability (72-120 hours post-transfection), baculovirus was harvested from the cell culture medium. Culture was removed from the cells and centrifuged at 250×g for 5 minutes to remove cells and large debris. Clarified supernatant was transferred to fresh conical tubes. This was the P1 viral stock. P1 viral stock was stored at 4° C., protected from light.

Viral titer was determined by baculovirus tittering assay. five 10-fold serial dilutions (dilution range: $1\times10^{-1}$ to $1\times10^{-5}$) of the P1 viral stock were prepared in fresh yeast lysate-free medium. Adapted Sf9 cells were diluted to $1.25\times10^6$ VCM in yeast lysate-free medium. Reactions were set up in a 24-well suspension plate as follows:

1. 1 mL of each serial dilution (other than the first dilution, $1\times10^{-7}$) were added to appropriate wells (1 well per dilution).
2. 1 mL fresh yeast lysate-free medium was added to a negative control (i.e., no virus) well.
3. 800 µL of cells at $1.25\times10^6$ viable cells/well was added to wells containing each dilution as well as the negative control well. Any unused well was filled with 1 mL medium or PBS.
4. Plate was incubated overnight at 27° C. in a non-humidified incubator on a shaking platform set to 225±5 rpm.

The following reagents were prepared:
Dilution Buffer: PBS containing 2% fetal bovine serum (FBS).
Anti-baculovirus envelope gp64 APC antibody: Antibody was diluted in dilution buffer to a final concentration of 0.15 µg/mL.

The samples were prepared for analysis by flow cytometry:
a. After 14-16 hours of incubation, the 24-well suspension plate was removed from the incubator and the contents of each well transferred to into separate FACS tubes, one FACS tube per well.
b. The tubes were centrifuged at 300×g for 5 minutes. Supernatants were carefully aspirated and discarded.
c. Each cell pellet was resuspended in 100 µL diluted antibody and mixed briefly by vortexing for 3-5 seconds.
d. Tubes were incubated at room temperature for 30 minutes.
e. Samples were washed by adding 1 mL PBS followed by centrifugation at 300×g for 10 minutes. Supernatants were carefully aspirated and discarded.
f. Each cell pellet was resuspended in 1 mL dilution buffer.

The samples were analyzed on a flow cytometer (Red Laser—Excitation: 633-647 nm; Emission: 660 nm). Percent positive gp64-expressing cells were recorded for each dilution and negative control samples.

The virus titer was determined:
a. The dilution sample that yielded percent gp64-positive cells of <10% was chosen.
b. Using the cell number per well (i.e., $1\times10^6$ cells/mL), the optimum dilution sample, and the percent gp64-positive cells in that respective dilution sample, viral titer was calculated using the equation below:

$$\text{Viral Titer}\left(\frac{ivp}{mL}\right) = \left(\frac{\text{Cell number} \times \text{Percent } gp64 \text{ positive cells}}{\text{Dilution of virus stock}}\right) \times 0.01$$

c. Multiplicity of Infection (MOI) is defined as the number of virus particles per cell.

The following formula was used to calculate how much viral stock (inoculum) to add to obtain a specific MOI:

$$\text{Amount of virus required} = \frac{MOI \times \text{number of cells}}{\text{titer of virus stock}\left(\frac{ivp}{ml}\right)}$$

Results

Figure 1B:
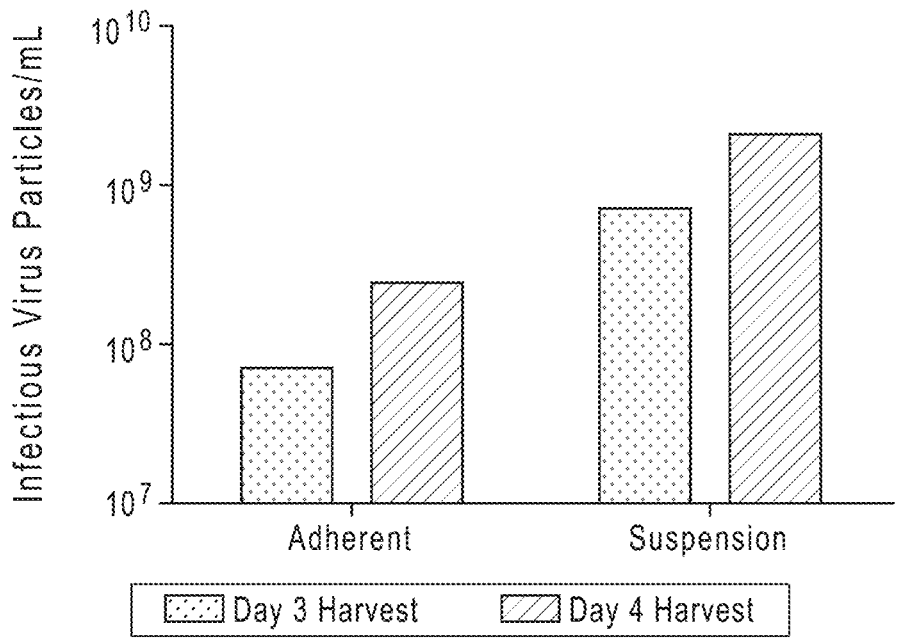
FIG. 1B is a bar graph showing the amount of baculovirus isolated from Sf9 cells grown in chemically-defined, yeast lysate-free insect cell medium as adherent culture or suspension culture.

As indicated in FIG. 1B, adapted Sf9 cells grown in suspension culture produced higher infectious particles per mL than cells grown in adherent culture, at both day 3 and day 4 post-transfection.

Example 4: Protein Expression in Adapted Sf9 Cells

Adapted Sf9 cells were subcultured and expanded until they reached a density of approximately $5\times10^6$-$10\times10^6$ viable cells/mL and >90% viability. On the day prior to infection, cells were seeded to a final density of $5\times10^6$ viable cells/mL with fresh yeast lysate-free medium, pre-warmed to room temperature. The flask was gently swirled to mix the cells. Immediately after seeding, the protein enhancer was added to the shake flasks (see Table 1). The cells were incubated overnight in a 27° C. non-humidified, air regulated non-$CO_2$ atmosphere incubator on an orbital shaker platform.

TABLE 1

Volumes for Protein Expression at Various Scales

| | Flask Size | | | |
|---|---|---|---|---|
| | 125 mL | 250 mL | 500 mL | 1 L |
| Total number of cells | $1.25 \times 10^8$ | $2.5 \times 10^8$ | $5 \times 10^8$ | $10 \times 10^8$ |
| Final cell density | $5 \times 10^6$ cells/mL | $5 \times 10^6$ cells/mL | $5 \times 10^6$ cells/mL | $5 \times 10^6$ cells/mL |
| Initial culture volume | 25 mL | 50 mL | 100 mL | 200 mL |
| Protein enhancer | 100 µL | 200 µL | 400 µL | 800 µL |
| Volume of baculovirus stock | 250-500 µL | 500-1000 µL | 1-2 mL | 2-4 mL |
| MOI | 5 | 5 | 5 | 5 |
| Shaker Speed | 125 ± 5 rpm for shakers with a 19-mm orbit | | | |
| | 120 ± 5 rpm for shakers with a 25-mm orbit | | | |
| | 95 ± 5 rpm for shakers with a 50-mm orbit | | | |
| Flask type | Non-baffled, Vented | | | |

Viable cell density and viability was determined 18-24 hours after addition of the protein enhancer. Cell density was approximately $5\times10^6$-$7\times10^6$ viable cells/mL and ≥80% viability. Cells were infected using high-titer virus stock at an MOI of 5 (see Table 1). Cells were incubated in a 27° C. non-humidified, air regulated non-$CO_2$ atmosphere incubator on an orbital shaker platform, at the speed indicated in Table 1.

Protein was harvested from cells (or media, if recombinant protein is secreted) at 24-120 hours post-infection.

Results

Figure 2A:
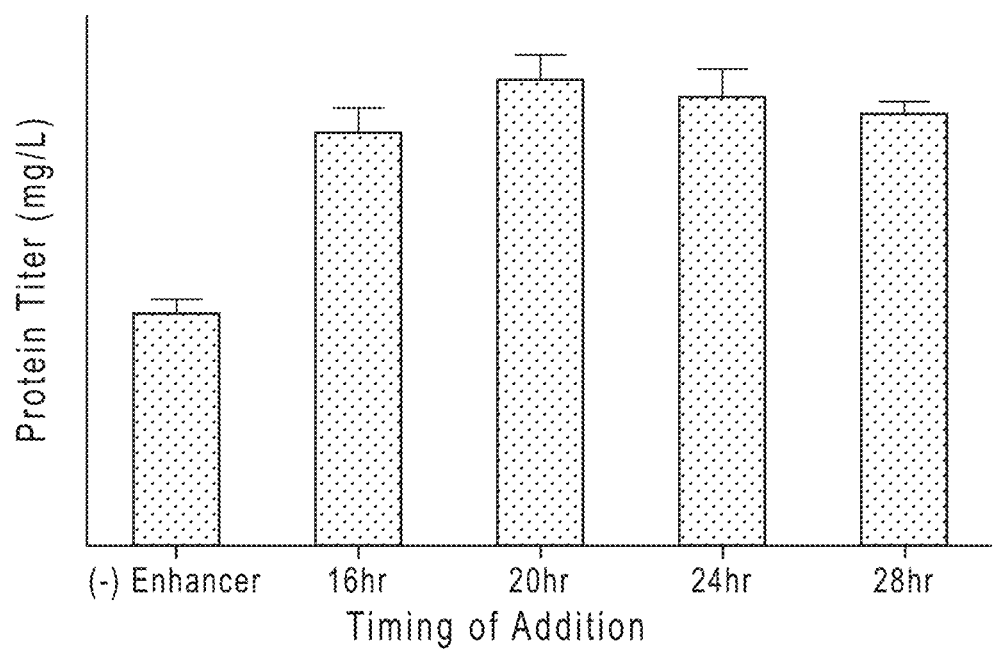
FIG. 2A is a bar graph showing the protein titer from Sf9 cells grown in chemically-defined, yeast lysate-free insect cell medium with no protein enhancer ((−) Enhancer) or protein enhancer added 16, 20, 24, or 28 hours prior to infection with protein-expressing baculovirus.
Figure 2B:
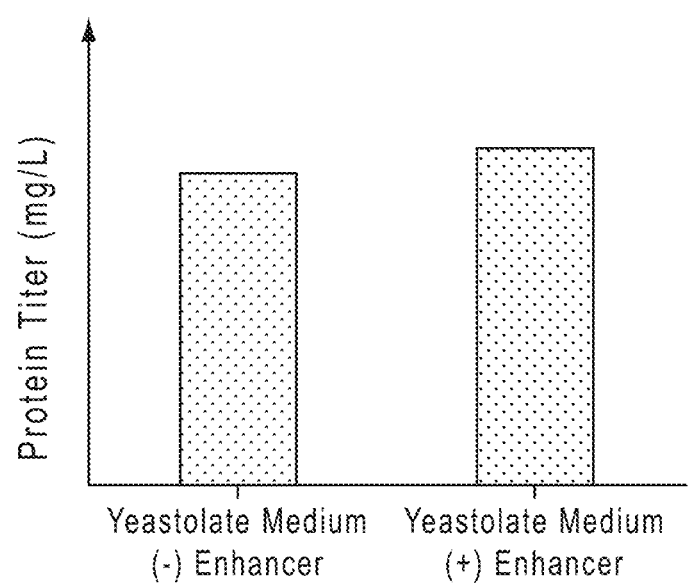
FIG. 2B is a bar graph showing the protein titer from Sf9 cells grown in insect cell medium containing yeast lysate, with or without addition of the protein enhancer.

The optimal time point for addition of the protein enhancer was determined using the above protocol, with addition of the protein enhancer at the indicated time point prior to infection. FIG. 2A shows the protein titer (mg/mL) produced by adapted Sf9 cells when the protein enhancer was added at 16 hours, 20 hours, 24 hours, or 28 hours prior to infection with baculovirus. Titer at all time points was greater than cells grown without protein enhancer ((−) Enhancer). Incubation with protein enhancer did not affect protein titer from Sf9 cells grown in medium containing yeast lysate (FIG. 2B).

Figure 3A:
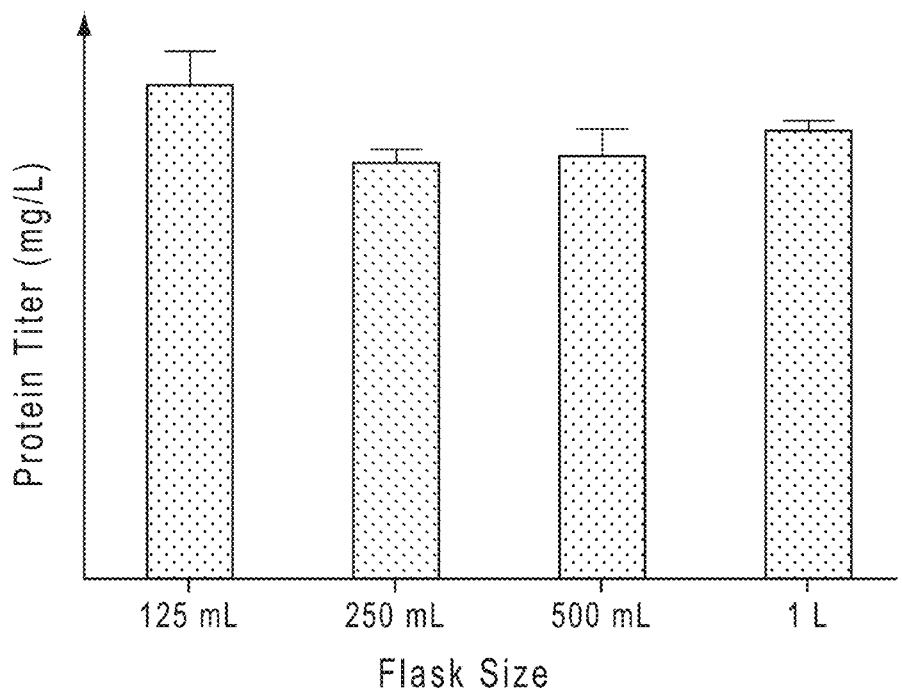
FIG. 3A is a bar graph showing protein titer from baculovirus-infected Sf9 cells grown in chemically-defined, yeast lysate-free insect cell medium in the indicated sized flask.

Protein titer as a function of flask/culture size was evaluated by growing the adapted Sf9 cells in 125 mL, 250 mL, 500 mL, or 1 L flasks during infection and protein production, using the medium (culture), enhancer, and baculovirus stock volumes indicated in Table 2. Protein titers are indicated in FIG. 3A. These results indicate that this protein expression protocol is directly scalable from 125 mL to 1 L flask scale.

TABLE 2

Parameters by Flask Size

| Flask size | 125 mL | 250 mL | 500 mL | 1 L |
|---|---|---|---|---|
| Culture Volume | 25 mL | 50 mL | 100 mL | 200 mL |
| Enhancer Volume | 100 μL | 200 μL | 400 μL | 800 μL |
| Baculovirus Stock Volume | 500 μL | 1 mL | 2 mL | 4 mL |
| Shake Speed | 125 rpm | | | |

Figure 3B:
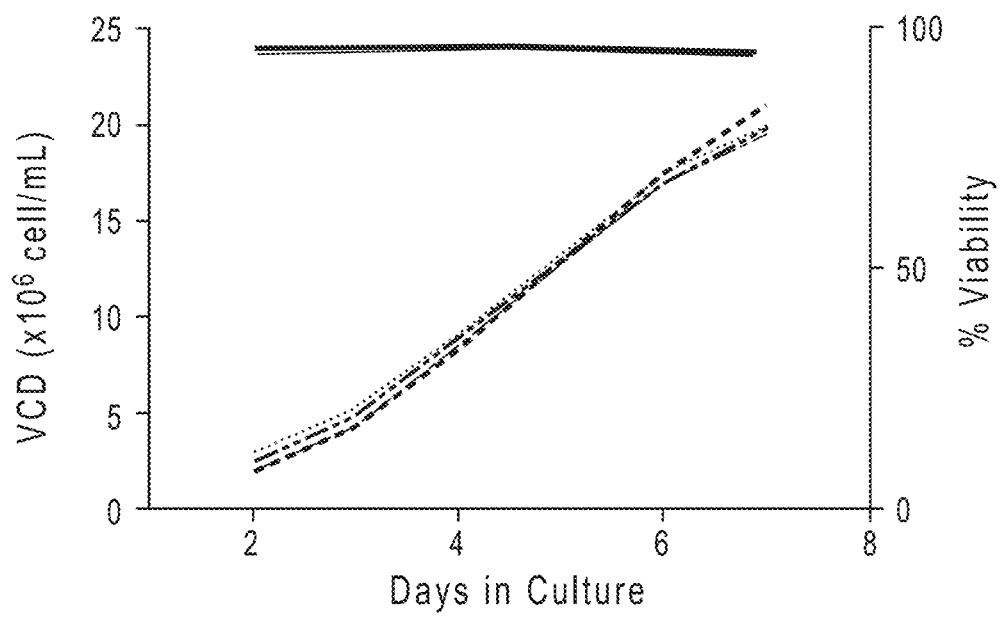
FIG. 3B is a line graph showing viable cell density (VCD; solid lines) and percent viability (dashed lines) of uninfected cells grown in the indicated sized flask.
Figure 3C:
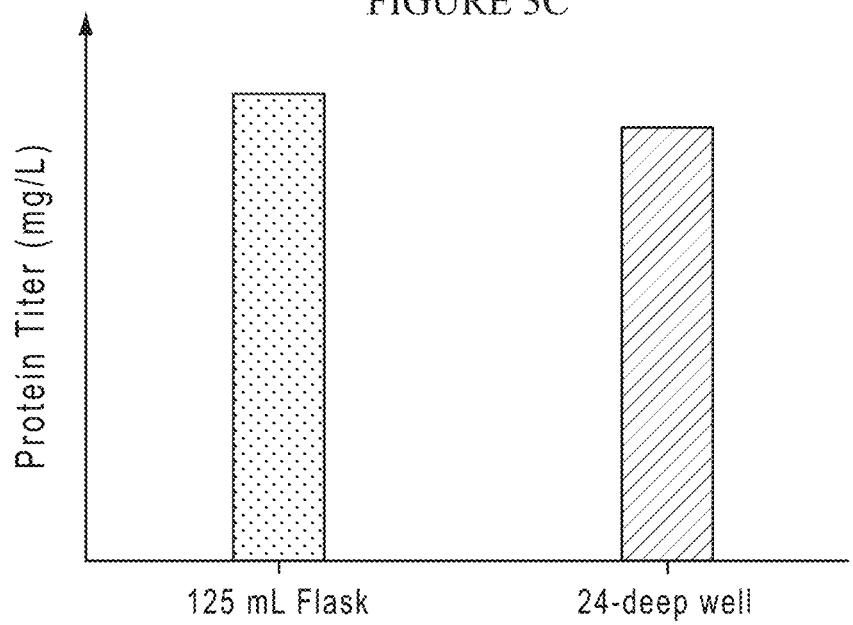
FIG. 3C is a bar graph showing the protein titer from baculovirus-infected Sf9 cells grown in chemically-defined, yeast lysate-free insect cell medium in a 125 mL flask or a 24 deep well plate.

As shown in FIG. 3C, the protein expression protocol can also be scaled down to 24 deep well plates (final culture volume approximately 4 mL, enhancer volume 16 μL, baculovirus stock volume 80 μL, and shake speed of 250 rpm).

Figure 3D:
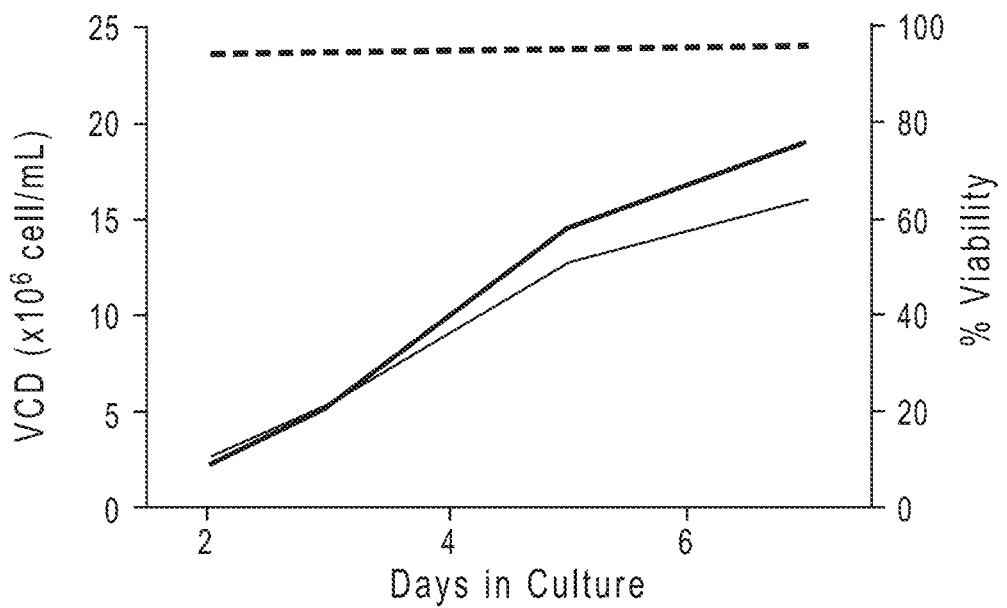
FIG. 3D is a line graph showing viable cell density (VCD; solid lines) and percent viability (dashed lines) of uninfected cells grown in the indicated sized container.

Viable cell density (VCD) and percent viability for uninfected cells cultured in each sized container over 2-7 days in culture are indicated in FIGS. 3B and 3D.

Figure 4A:
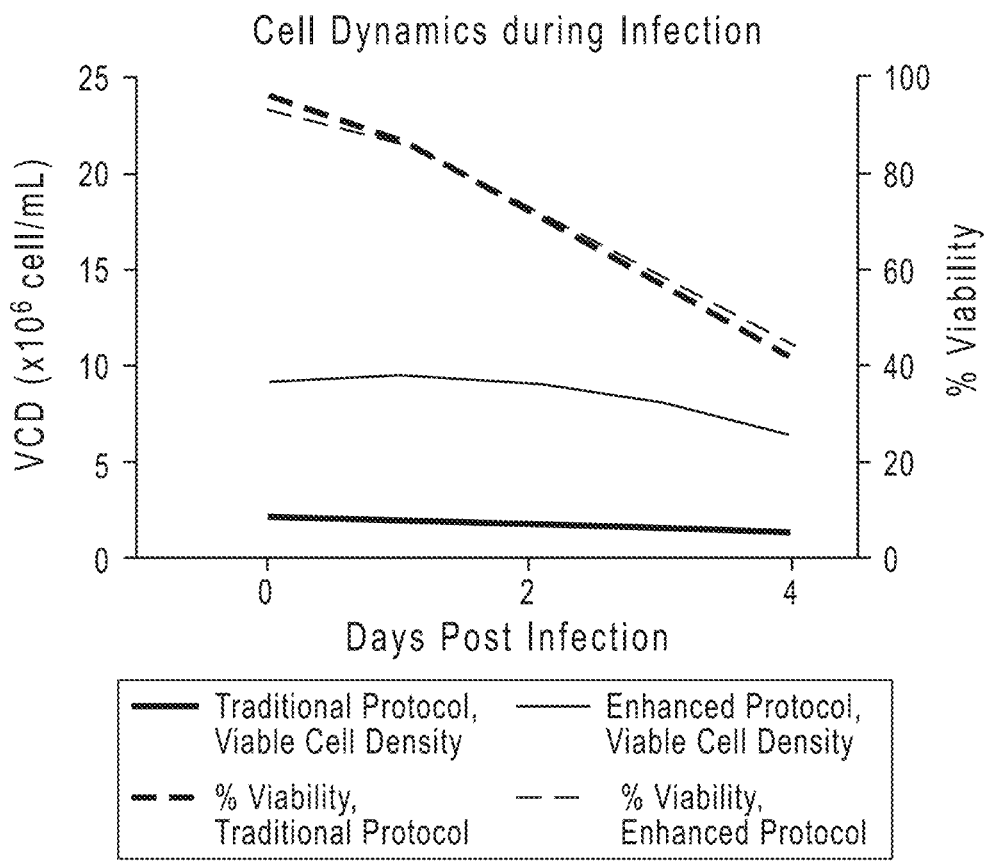
FIG. 4A is a line graph showing viable cell density (VCD; solid lines) and percent viability (dashed lines) of baculovirus-infected Sf9 cells grown in chemically-defined, yeast lysate-free insect cell medium as described herein ("enhanced protocol"; light) compared to baculovirus-infected Sf9 cells grown in insect cell medium containing yeast lysate ("traditional protocol"; heavy).
Figure 4B:
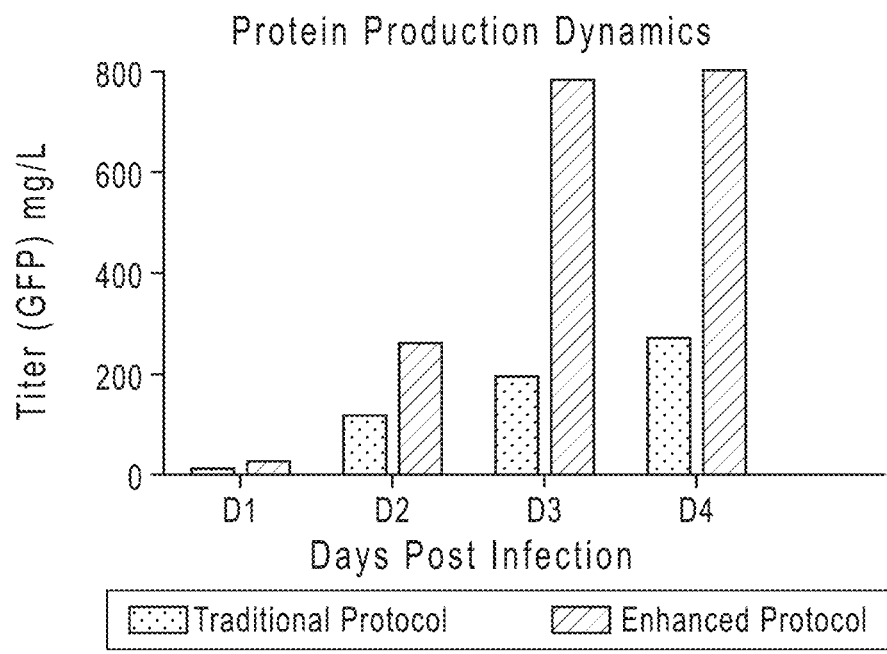
FIG. 4B is a bar graph showing the protein titer 1, 2, 3, and 4 days post-infection of the cells from FIG. 4A.

Cell viability and protein production dynamics were determined for multiple proteins, comparing a "traditional protocol" (Sf9 cells grown in yeast lysate-containing insect cell medium, without protein enhancer) with the enhanced protocol described herein. FIG. 4A shows the cell viability after infection with green fluorescent protein (GFP)-expressing baculovirus for the traditional (heavy lines) and enhanced (light lines) protocols. FIG. 4B shows GFP titer (mg/L) on days 1 through 4 post-infection for traditional (dotted bars) and enhanced (diagonal bars) protocols.

Figure 5A:
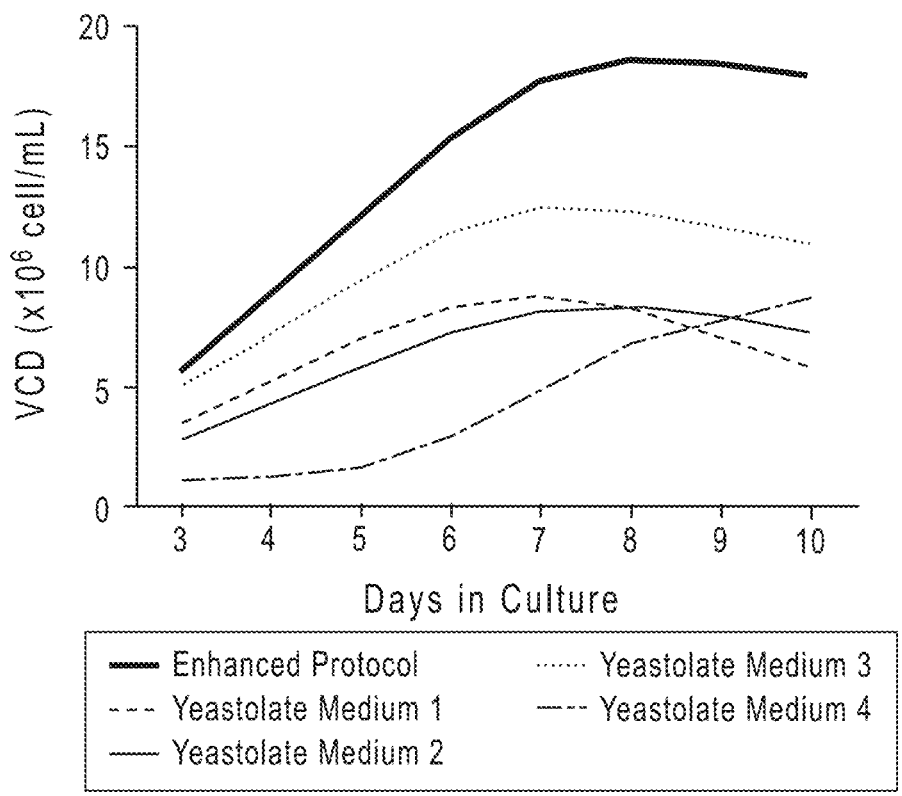
FIG. 5A is a line graph showing viable cell density (VCD) of baculovirus-infected Sf9 cells grown in chemically-defined, yeast lysate-free insect cell medium as described herein ("enhanced protocol"; solid) compared to baculovirus-infected Sf9 cells grown in four different insect cell media containing yeast lysate, as indicated.
Figure 5B:
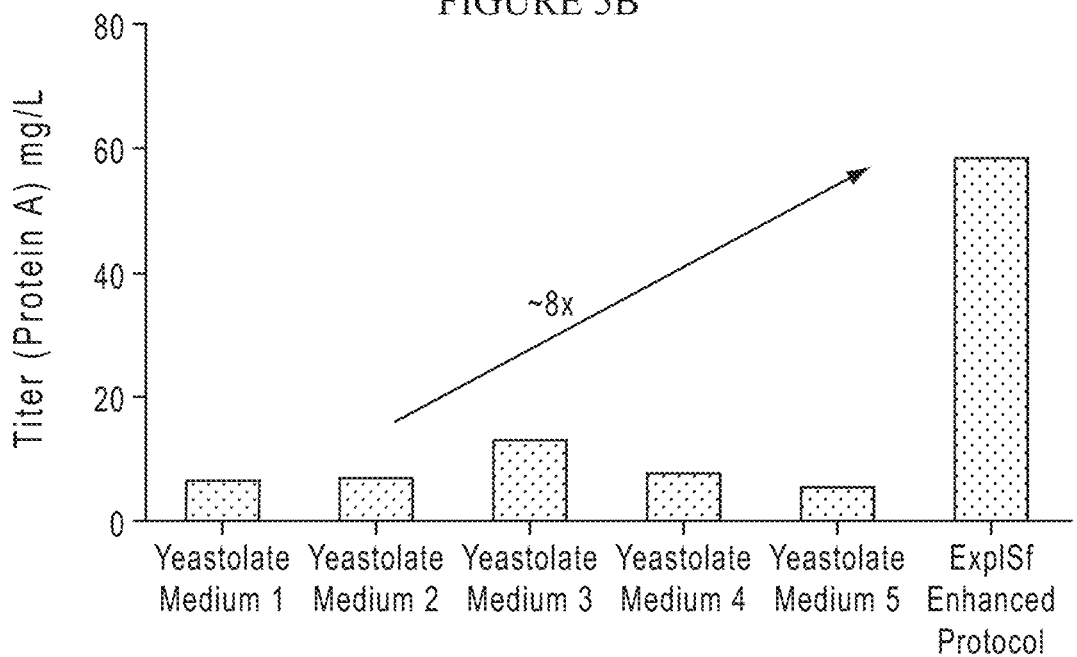
FIGS. 5B-5D are bar graphs showing the titer of proteins harvested from baculovirus-infected Sf9 cells grown in chemically-defined, yeast lysate-free insect cell medium as described herein ("enhanced protocol") compared to baculovirus-infected Sf9 cells grown in the four different insect cell media containing yeast lysate from FIG. 5A.
Figure 5C:
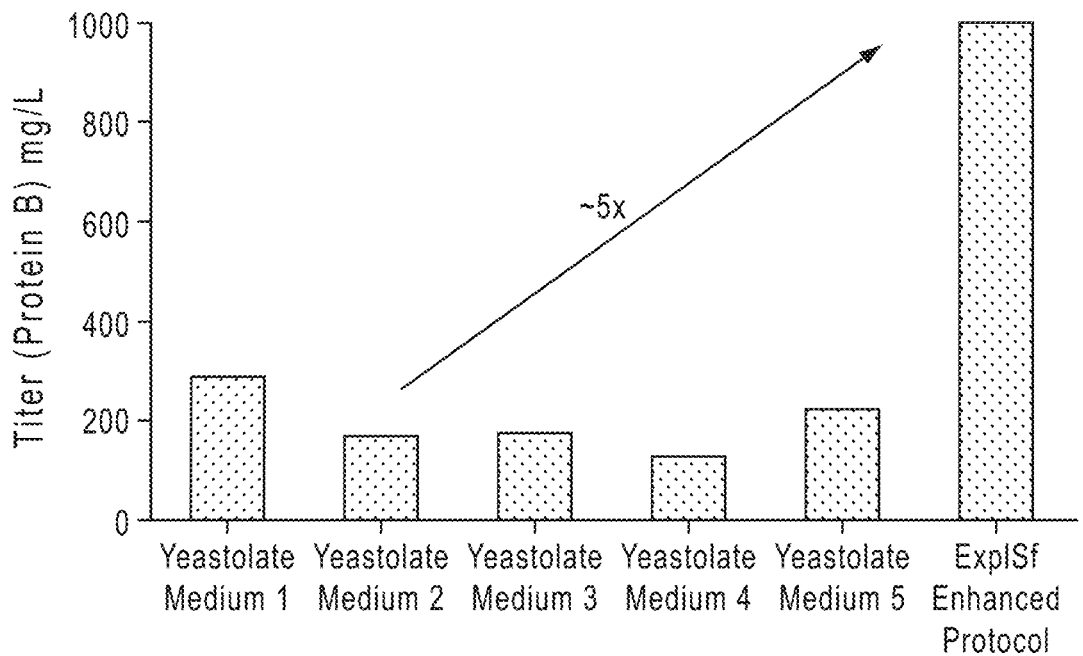
Figure 5D:
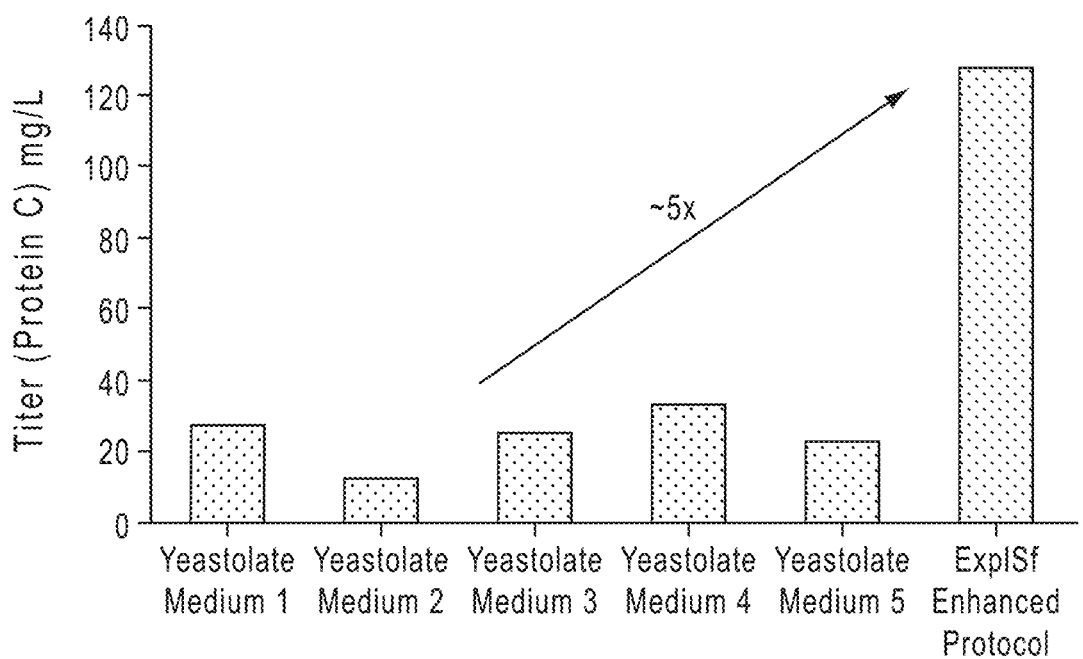

Baculovirus-mediated protein production in Sf9 cells grown in multiple yeast lysate-containing mediums was compared to the enhanced protocol described herein. The enhanced protocol provided better cell viability (FIG. 5A) and approximately 5 to 8 times higher protein production from multiple protein-expressing baculovirus constructs (FIGS. 5B-5D).

Figure 6A:
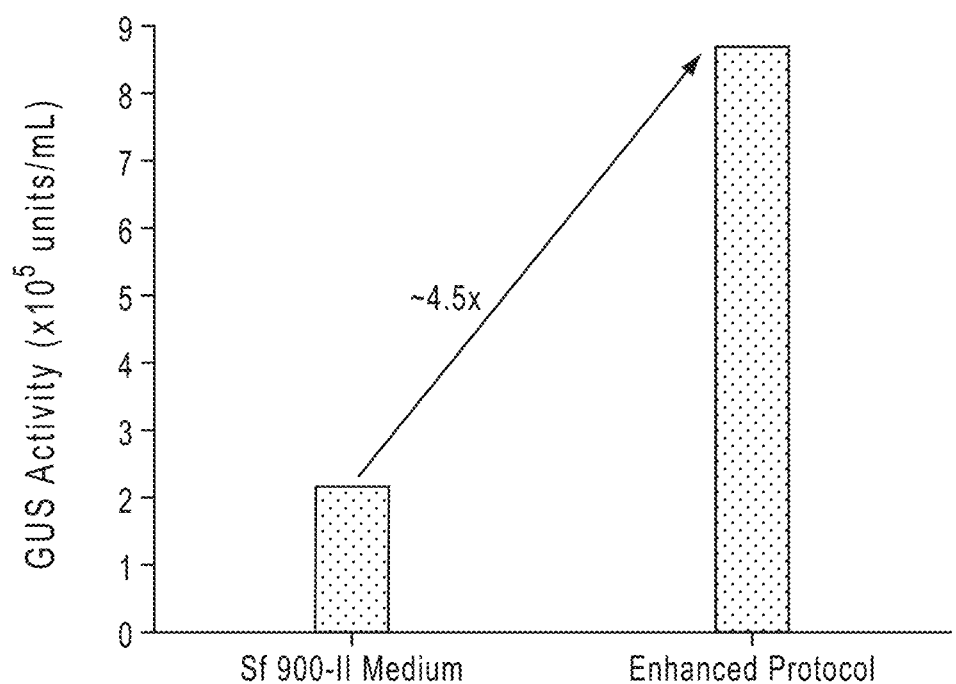
FIG. 6A is a bar graph showing β-glucuronidase (GUS) activity from Sf9 cells infected with GUS-expressing baculovirus and grown in chemically-defined, yeast lysate-free insect cell medium as described herein ("enhanced protocol") compared to baculovirus-infected Sf9 cells grown in Sf900-II insect cell medium containing yeast lysate.
Figure 6B:
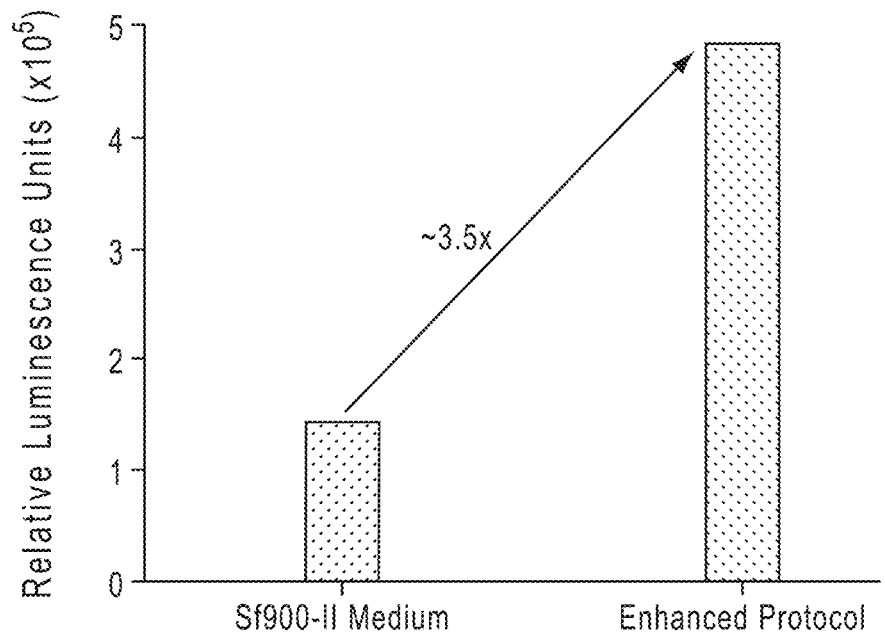
FIG. 6B is a bar graph showing secreted alkaline phosphatase (SEAP) activity from Sf9 cells infected with SEAP-expressing baculovirus and grown in chemically-defined, yeast lysate-free insect cell medium as described herein ("enhanced protocol") compared to baculovirus-infected Sf9 cells grown in Sf900-II insect cell medium containing yeast lysate.
Figure 6C:
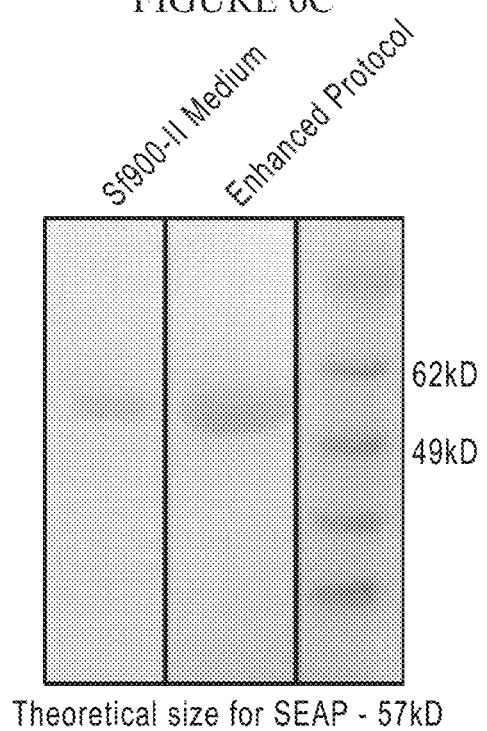
FIG. 6C is a photograph of polyacrylamide gel electrophoresis of SEAP from the cells described in FIG. 6B.
Figure 6D:
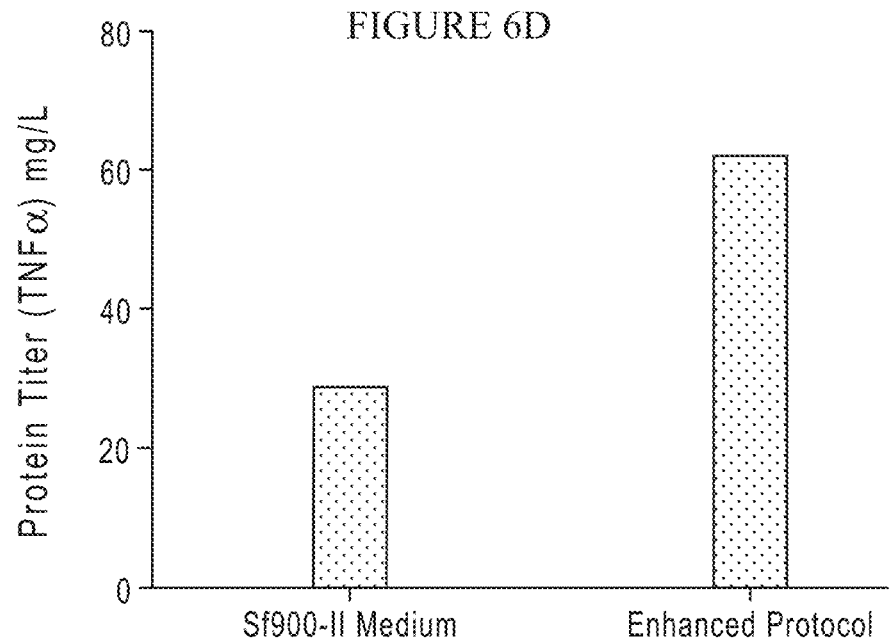
FIG. 6D is a bar graph showing tumor necrosis factor-alpha (TNF-α) protein titer from Sf9 cells infected with TNF-α-expressing baculovirus and grown in chemically-defined, yeast lysate-free insect cell medium as described herein ("enhanced protocol") compared to baculovirus-infected Sf9 cells grown in Sf900-II insect cell medium containing yeast lysate.

Baculovirus-mediated protein production in Sf9 cells grown in Sf-900™ II insect cell medium (ThermoFisher Scientific) was compared to the enhanced protocol described herein. Expression of β-glucuronidase (GUS), as determined by GUS activity (FIG. 6A); secreted alkaline phosphatase (SEAP), based on relative luminescence (FIG. 6B) and polyacrylamide gel electrophoresis (FIG. 6C); and tumor necrosis factor-alpha (TNF-α), as determined by protein titer (FIG. 6D) were all at least 2-fold higher using the enhanced protocol.

Figure 6E:
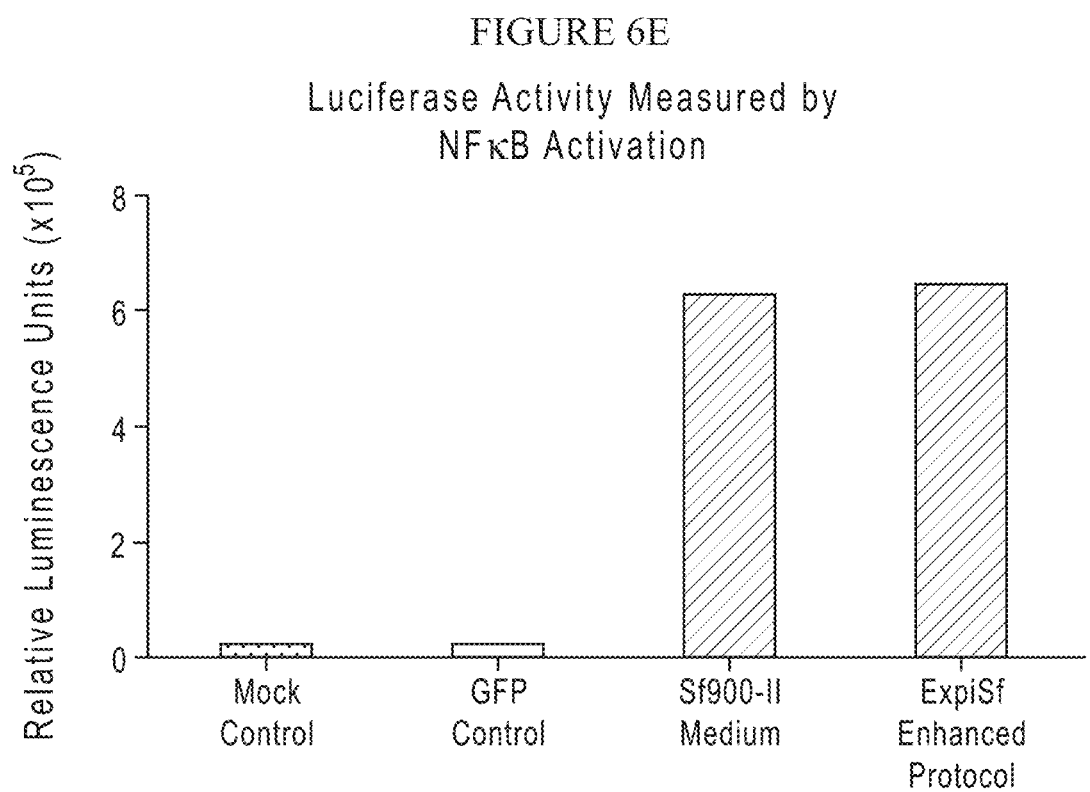
FIG. 6E represents activity of the TNF-α protein as measured in a nuclear factor kappa B (NFκB) luciferase assay.

Activity of the recombinant TNF-α protein was measured in a nuclear factor kappa B (NFκB) luciferase assay. Briefly, reporter cells containing an integrated luciferase reporter construct that is regulated by the NFκB response element were treated with TNF-α, and luciferase activity was measured. TNF-α protein activity was similar regardless of the protocol used to produce the TNF-α protein (FIG. 6E).

What is claimed is:

1. A baculovirus expression system comprising:
   (a) an insect cell medium, wherein the insect cell medium comprises an energy source selected from maltose, sucrose, glucose, trehalose, fructose, mannose, lactose, galactose, dextrose, or combinations thereof; and
   (b) a plurality of Sf9 cells.

2. The baculovirus expression system of claim 1, further comprising a protein expression enhancer.

3. The baculovirus expression system of claim 2, wherein the protein expression enhancer comprises a histone deacetylase (HDAC) inhibitor.

4. The baculovirus expression system of claim 3, wherein the HDAC inhibitor is selected from apicidin, belinostat, CI-994, CRA-024781, curcumin, panobinostat, sodium butyrate, sodium phenylbutyrate, suberoylanilide hydroxamic acid, trichostatin A, and valproic acid.

5. The baculovirus expression system of claim 3, wherein the HDAC inhibitor is sodium butyrate, sodium phenylbutyrate, trichostatin A, or valproic acid.

6. The baculovirus expression system of claim 1, further comprising a transfection reagent.

7. The baculovirus expression system of claim 6, wherein the transfection reagent is a cationic lipid transfection reagent.

8. The baculovirus expression system of claim 7, wherein the cationic lipid transfection reagent comprises at least one neutral lipid.

9. The baculovirus expression system of claim 6, wherein the transfection reagent is a polymer-based transfection reagent.

10. The baculovirus expression system of claim 9, wherein the polymer-based transfection reagent comprises at least one cationic polymer.

11. The baculovirus expression system of claim 1, wherein the plurality of Sf9 cells are capable of growing in suspension culture in the medium.

12. The baculovirus expression system of claim 11, wherein the plurality of Sf9 cells are capable of high-density growth in the medium.

13. The baculovirus expression system of claim 12, wherein the Sf9 cells are capable of peak cell density of about $2 \times 10^6$ to about $2 \times 10^8$ cells per milliliter (cells/mL).

14. The baculovirus expression system of claim 1, further comprising a baculovirus vector.

15. The baculovirus expression system of claim 1, wherein the insect cell medium does not comprise protein.

16. The baculovirus expression system of claim 1, wherein the insect cell medium does not comprise an ingredient obtained from an animal.

17. The baculovirus expression system of claim 1, wherein the insect cell medium comprises an inorganic salt selected from a barium salt, a cadmium salt, a copper salt, a magnesium salt, a manganese salt, a nickel salt, a potassium salt, a calcium salt, a silver salt, a tin salt, a zirconium salt, a sodium salt, or combinations thereof.

18. The baculovirus expression system of claim 1, wherein the insect cell medium comprises a vitamin selected from para-aminobenzoic acid, vitamin B12, biotin, choline, folic acid, inositol, nicotinic acid, niacinamide, pantothenic acid, pyridoxine, riboflavin, thiamine, a tocopherol, or combinations thereof.

* * * * *